US010959777B2

(12) United States Patent
Gustavsson et al.

(10) Patent No.: US 10,959,777 B2
(45) Date of Patent: *Mar. 30, 2021

(54) LASER SHAVING

(71) Applicant: Skarp Technologies (Delaware) Inc., Newport Beach, CA (US)

(72) Inventors: Morgan Lars Ake Gustavsson, Newport Beach, CA (US); Kyle McCormick, San Diego, CA (US); Paul William Binun, Chula Vista, CA (US)

(73) Assignee: Skarp Technologies (Delaware) Inc., Newport Beach, CA (US)

( * ) Notice: Subject to any disclaimer, the term of this patent is extended or adjusted under 35 U.S.C. 154(b) by 3 days.

This patent is subject to a terminal disclaimer.

(21) Appl. No.: 16/164,611

(22) Filed: Oct. 18, 2018

(65) Prior Publication Data
US 2019/0247119 A1  Aug. 15, 2019

Related U.S. Application Data

(63) Continuation of application No. 15/342,064, filed on Nov. 2, 2016, now Pat. No. 10,105,182, which is a
(Continued)

(51) Int. Cl.
*A61B 18/20* (2006.01)
*A61B 18/22* (2006.01)
*A61B 18/00* (2006.01)

(52) U.S. Cl.
CPC .......... *A61B 18/201* (2013.01); *A61B 18/203* (2013.01); *A61B 18/22* (2013.01);
(Continued)

(58) Field of Classification Search
CPC ........... A61B 2018/00476; A61B 2018/00779; A61B 2018/202; A61B 2018/2261; A61B 18/203; A61B 18/22
See application file for complete search history.

(56) References Cited

U.S. PATENT DOCUMENTS 4,617,926 A  10/1986  Sutton
5,606,798 A   3/1997  Kelman
(Continued)

FOREIGN PATENT DOCUMENTS

JP  S62-502724  10/1987
JP  H5-509028   12/1993
(Continued)

OTHER PUBLICATIONS

Jul. 4, 2014 International Search Report and Written Opinion for Application No. PCT.US2014/027674 filed Mar. 14, 2014.
Extended Search Report in EP Application No. 14764647.5 dated Aug. 8, 2016 in 7 pages.

*Primary Examiner* — Scott Luan
(74) *Attorney, Agent, or Firm* — Knobbe Martens Olson & Bear, LLP

(57) ABSTRACT

A device configured to cut hair using laser light includes a handle portion and a shaving portion. The handle portion includes a battery and a laser light source. The laser light source is coupled to and configured to receive power from the battery. The laser light source is also configured to generate laser light having a wavelength selected to target a predetermined chromophore to effectively cut a hair shaft. The shaving portion includes a support and a single fiber optic supported by the support. The fiber optic has a proximal end, a distal end, an outer wall, and a cutting region positioned towards the distal end and extending along a portion of the side wall. The fiber optic is positioned to receive the laser light from the laser light source at the proximal end, conduct the laser light from the proximal end toward the distal end, and emit the light out of the cutting region and toward hair when the cutting region is brought in contact with the hair.

27 Claims, 15 Drawing Sheets

Related U.S. Application Data continuation-in-part of application No. 14/694,994, filed on Apr. 23, 2015, now Pat. No. 9,532,834, which is a continuation of application No. 14/210,248, filed on Mar. 13, 2014, now Pat. No. 9,017,322.

(60) Provisional application No. 62/405,172, filed on Oct. 6, 2016, provisional application No. 62/396,047, filed on Sep. 16, 2016, provisional application No. 62/249,704, filed on Nov. 2, 2015, provisional application No. 61/801,162, filed on Mar. 15, 2013.

(52) U.S. Cl.
CPC ............... *A61B 2018/00476* (2013.01); *A61B 2018/00702* (2013.01); *A61B 2018/00732* (2013.01); *A61B 2018/00779* (2013.01); *A61B 2018/202* (2013.01); *A61B 2018/2023* (2017.05); *A61B 2018/225* (2013.01); *A61B 2018/2205* (2013.01); *A61B 2018/2244* (2013.01); *A61B 2018/2261* (2013.01); *A61B 2018/2266* (2013.01); *A61B 2018/2288* (2013.01)

(56) References Cited

U.S. PATENT DOCUMENTS

| | | | |
|---|---|---|---|
| 5,735,844 A * | 4/1998 | Anderson | ............ A61B 18/203 606/9 |
| 6,030,378 A | 2/2000 | Stewart | |
| 6,129,723 A | 10/2000 | Anderson et al. | |
| 6,533,775 B1 | 3/2003 | Rizoiu | |
| 9,017,322 B2 | 4/2015 | Gustavsson et al. | |
| 9,532,834 B2 | 1/2017 | Gustavsson et al. | |
| 2006/0293728 A1* | 12/2006 | Roersma | ............ A61N 5/0617 607/88 |
| 2008/0201954 A1 | 8/2008 | Meinschien | |
| 2008/0244912 A1 | 10/2008 | Gustavsson | |
| 2009/0264872 A1 | 10/2009 | Van Hal et al. | |
| 2012/0123444 A1 | 5/2012 | Verhagen et al. | |

FOREIGN PATENT DOCUMENTS

| | | |
|---|---|---|
| JP | 2005-511196 | 4/2005 |
| JP | 2009-508611 | 3/2009 |
| KR | 1020080057241 A | 6/2008 |
| KR | 1020120049285 A | 5/2012 |
| RU | 2106791 | 3/1998 |
| WO | WO 1986/05676 | 10/1986 |
| WO | WO 93/05920 | 1/1993 |

* cited by examiner

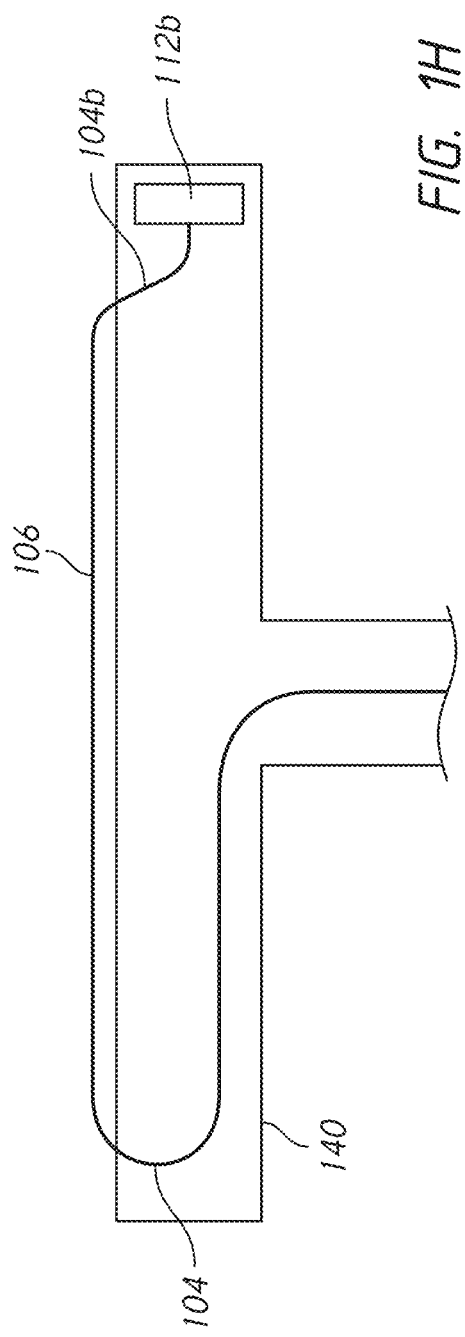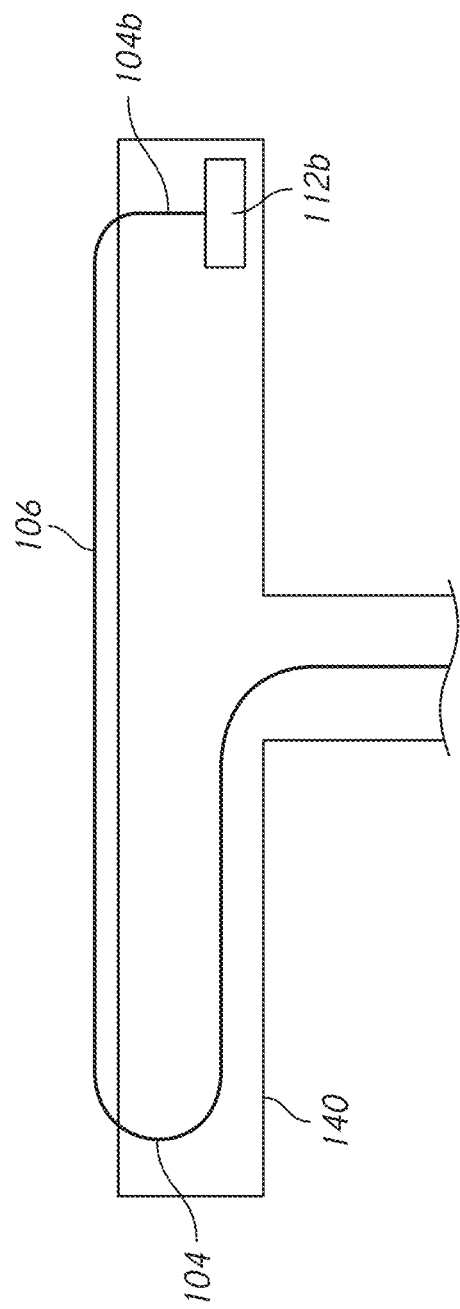

LASER SHAVING

CROSS-REFERENCE TO RELATED APPLICATIONS

The present application is a continuation of U.S. application Ser. No. 15/342,064, filed Nov. 2, 2016, which is a continuation-in-part of U.S. application Ser. No. 14/694,994, filed Apr. 23, 2015, which is a continuation of U.S. application Ser. No. 14/210,248, filed Mar. 13, 2014, now U.S. Pat. No. 9,017,322, which claims the priority benefit of U.S. Provisional No. 61/801,162, filed Mar. 15, 2013. U.S. application Ser. No. 15/342,064 also claims the priority benefit of U.S. Provisional No. 62/249,704, filed Nov. 2, 2015, U.S. Provisional No. 62/396,047, filed Sep. 16, 2016, and U.S. Provisional No. 62/405,172, filed Oct. 6, 2016. All of the foregoing are incorporated by reference in their entireties.

BACKGROUND

Field

The present disclosure generally relates to devices and methods for cutting or processing matter using light, including but not limited to shaving using laser light.

Description of the Related Art

Shaving is most commonly performed using razors having one or more metal blades. However, razors can irritate and damage the user's skin. Razors are also limited to removing hair at the surface of the skin, which results in the hair becoming visible again in a relatively short time period. Various laser devices are also available for hair removal. However, laser hair removal devices and methods typically involve using laser light to destroy the hair follicle below the skin surface for permanent or semi-permanent hair removal. Such devices and methods are typically more dangerous, expensive, unsuitable for home use, and often do not provide effective cutting of lighter colored hair.

SUMMARY

The present disclosure describes devices and methods for cutting matter, including but not limited to shaving hair. In some embodiments, a shaving device uses electromagnetic radiation or light (e.g., laser or other light energy) to cut or damage one or more hair shafts. At least one surface of at least one fiber or a light guide can emit light towards at least one hair shaft. In some embodiments, the fiber or light guide is configured to couple light into at least one hair shaft through at least one light transmitting surface of the fiber or light guide. Such devices can couple light into one or more hair shafts with or without a coupling enhancing medium, such as any such coupling medium described below, or others. Devices according to the present disclosure can be effective, efficient, cost effective, and safe for home use.

In one embodiment, a device configured to cut hair using laser light includes a handle portion and a shaving portion. The handle portion includes a battery and a laser light source. The laser light source is coupled to and configured to receive power from the battery. The laser light source is also configured to generate laser light having a wavelength selected to target a predetermined chromophore to effectively cut a hair shaft. The shaving portion includes a support and a single fiber optic supported by the support. The fiber optic has a proximal end, a distal end, an outer wall, and a cutting region positioned towards the distal end and extending along a portion of the side wall. The fiber optic is positioned to receive the laser light from the laser light source at the proximal end, conduct the laser light from the proximal end toward the distal end, and emit the light out of the cutting region and toward hair when the cutting region is brought in contact with the hair.

The fiber optic may be further configured to prevent light from being emitted from the cutting region when the cutting region is not in contact with the hair. The support may be T-shaped. The support may include a channel configured to receive the fiber optic, and the fiber optic may be positioned within the channel. In some embodiments, the wavelength is within one or more ranges selected from a group consisting of: 380 nm to 480 nm, 380 nm to 500 nm, 400 nm to 500 nm, 2500 nm to 3500 nm, 2950 nm to 3050 nm, and 2700 nm to 3500 nm.

In some embodiments, the shaving portion is removably coupled to the handle portion, the fiber optic is removably coupled to the support, or both. The predetermined chromophore may be selected from the group consisting of: sebum, a fatty acid, phytoshingosine, ceramide, cholesterol, cholesterol sulfate, and cholesterol oleate. In some embodiments, the predetermined chromophore may be selected from the group consisting of: melanin, pheomelanin, keratin and water. In some embodiments, the device also includes an optic configured to direct the laser light from the laser light source to the proximal end of the fiber optic.

In some embodiments, the fiber optic has a diameter in the range of about 4 microns to about 1000 microns. The device may also include a reflector positioned at the distal end of the fiber optic and configured to reflect light towards the fiber optic proximal end. The device may also include a vacuum source coupled to the support and configured to provide aspiration near the cutting region.

In some embodiments, the fiber optic includes a core and a cladding that surrounds the core along the fiber optic length, except at the cutting region. The cutting region may have a radius of curvature that is different than radius of curvature of the fiber optic near its proximal end. In some embodiments, a cross-sectional shape of the fiber optic at the cutting region is wedge-shaped. Other shapes are also possible (e.g., flat, rectangular solid, etc.). In some embodiments, the fiber optic tapers in diameter along the cutting region.

In yet another embodiment, a method of shaving hair with laser light includes providing a device configured to cut hair and directing laser light from the device's light source, through its cutting region, and towards a shaft of the hair to cut the hair. The device includes a handle portion and a shaving portion. The handle portion includes a battery and a laser light source. The laser light source is coupled to and configured to receive power from the battery. The laser light source is also configured to generate laser light having a wavelength selected to target a predetermined chromophore to effectively cut a hair shaft.

The shaving portion includes a support and a single fiber optic supported by the support. The fiber optic has a proximal end, a distal end, an outer wall, and a cutting region positioned towards the distal end and extending along a portion of the side wall. The fiber optic is positioned to receive the laser light from the laser light source at the proximal end, conduct the laser light from the proximal end toward the distal end, and emit the light out of the cutting region and towards the hair when the cutting region is brought in contact with the hair.

The method may also include preventing light from being emitted from the cutting region when the cutting region is not in contact with the hair. The method may also include removably coupling: (1) the shaving portion to the handle portion, (2) the fiber optic to the support, or (3) both. The wavelength may be within one or more ranges selected from a group consisting of: 380 nm to 480 nm, 380 nm to 500 nm, 400 nm to 500 nm, 400 nm to 700 nm, 2500 nm to 3500 nm, 2950 nm to 3050 nm, and 2700 nm to 3500 nm.

In some embodiments, an on-contact, side-emitting waveguide configured to cut matter, such as hair or organic tissue, has a first end configured to act as or be coupled to a support structure and a second end or portion exposed to air. The first end can have a low-index cladding. The second end can include a thin film deposited on at least a portion of the waveguide.

In some such embodiments, the thin film is optically clear. The thin film can include or be made of metal oxide, metal nitride, carbon, silicon, and/or other dielectric compounds. The film, or any one or more layers that make up the film, can have an optical index of refraction in the range of 0.5 to 3 times the index of the waveguide. The film can have a thickness in the range of 5 nm to 10,000 nm. The thickness of the film can be adjusted to control or affect coupling of light from the waveguide into the target (e.g., hair or organic tissue). In some embodiments, the thickness of the film has a gradient and/or pattern of thickness variation along a length of a cutting region of the waveguide. The film can be deposited on the waveguide by techniques such as ALD, PVD, CVD, and/or IBS. In some embodiments, the film has hydrophilic, hydrophobic, oleophilic, and/or oleophobic surface properties. The film can be photocatalytic.

In some embodiments, an on-contact, side-emitting waveguide configured to cut matter, such as hair or organic tissue, has a first end configured to act as or be coupled to a support structure and a second end or portion exposed to air. The first end can have a low-index cladding. The second end can include a thin film stack deposited on at least a portion of the waveguide.

In some such embodiments, the thin film stack is optically clear. The thin film stack can include or be made of metal oxide, metal nitride, carbon, silicon, and/or other dielectric compounds. The film stack, or any one or more layers that make up the film stack, can have an optical index of refraction in the range of 0.5 to 3 times the index of the waveguide. The film stack can have a thickness in the range of 5 nm to 10,000 nm. The thickness of the film stack can be adjusted to control or affect coupling of light from the waveguide into the target (e.g., hair or organic tissue). In some embodiments, the thickness of the film stack has a gradient and/or pattern of thickness variation along a length of a cutting region of the waveguide. The film stack can be deposited on the waveguide by techniques such as ALD, PVD, CVD, and/or IBS. In some embodiments, the film stack has hydrophilic, hydrophobic, oleophilic, and/or oleophobic surface properties. The film stack can be photocatalytic.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein. All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects and advantages of the present disclosure will be described with reference to the following drawings, which are illustrative but should not be limiting of the present disclosure.

FIGS. 1H and 1I illustrate examples of support portions of a laser shaving device;

DETAILED DESCRIPTION

Figure 1A:
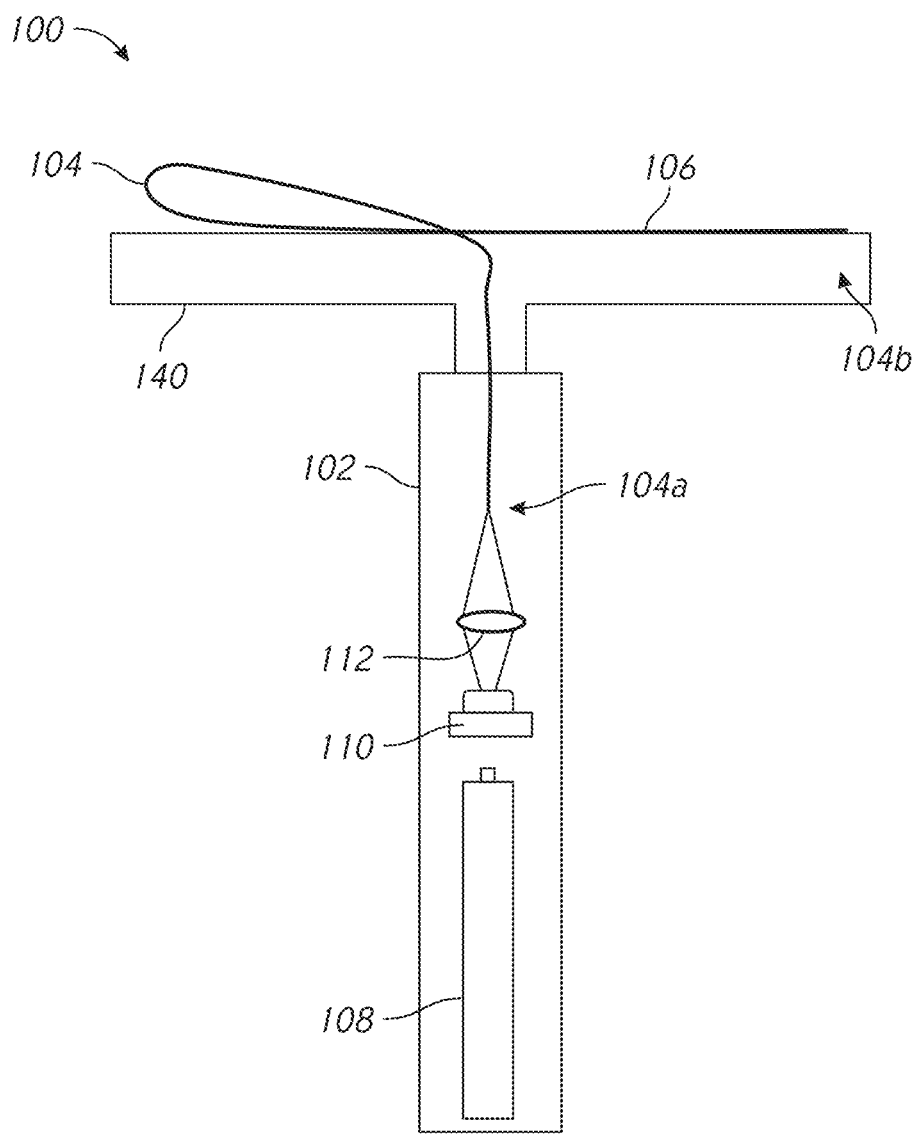
FIG. 1A illustrates an example embodiment of a laser shaving device.

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein should not be limited by any particular embodiments described below.

Hair shafts can be severed with high intensity light via absorption heating and burning and/or melting of the shaft. Some optical shaving devices based on this mechanism have been envisioned as an alternative to shaving with razors or laser hair removal. Some such devices include a plurality of optical fibers and are used to cut hair by coupling light into one end of the optical fibers and emitting the light out of the opposite end of the optical fibers and in a direction parallel to their longitudinal axes. One problem with using a plurality of optical fibers in this way is the increased loss of light into the cross-sectional area of the claddings of the multiple fibers. Light energy is lost in the cladding of a fiber as light travels through it, and therefore, more fiber optics results in more light energy loss. In addition, when coupling light from a single light source into a cross-sectional surface (e.g., the proximal end) of a plurality of fibers (e.g., a fiber-optic bundle), an additional problem is fraction losses into the spaces between the fibers, e.g. in the case of round fibers that are bundled together.

Devices and methods according to the present disclosure advantageously overcome these problems and disadvantages associated with cladding cross-sectional losses and/or fraction losses, resulting in a more efficient device. The techniques described herein advantageously allow the devices to be smaller, lighter, and/or less costly to manufacture. In addition, in some embodiments, a single light source is coupled into a single fiber-optic conduit. The single fiber-optic conduit is configured to emit light out of a predetermined area along the side of the fiber's outer wall, as discussed in greater detail below. The side of the fiber's outer wall may be conditioned or configured in a manner that light can only escape out of the side of the fiber's outer wall surface when the outer wall surface is brought into contact with hair. In such cases, intense, energy-focused light is emitted only at such contact locations. This side-firing, focusing effect advantageously results in being able to effectively cut hair (and more generally, to remove matter) using less energy. Therefore, in some embodiments, an efficient shaving device may include a battery powered, hand-held device. In addition, because light is only emitted out of the side of the fiber when in contact with hair (or other targeted matter), the device is safer than devices that continuously emit light out of their distal ends when activated. In addition, the light exiting a side-firing fiber-optic shaving device exits the fiber-optic at a larger divergence angle than an end-firing fiber-optic. Therefore, because of such larger divergence angle, the side-firing fiber-optic shaving device is safer than end-firing devices, as the light from a side-firing device will diverge quicker and become weaker in intensity and fluence (power and energy per area) over distance.

Additionally, to damage and/or cut one or more hair shafts with light, at least some of the light energy is absorbed by the hair shaft and converted into heat or induce a bond breaking mechanism. There are three chromophores in hair that substantially absorb light—melanin, keratin, and water. Keratin and water have absorption peaks at around 3000 nm. Melanin has an absorption peak around 300 nm, but remains relatively flat, decreasing almost linearly (on a logarithmic scale) to about 3000 nm. Darker hair, for example, black and brown hair, contains melanin and can be damaged or cut by sufficient amounts of ultraviolet (UV), visible (VIS), near infrared (NIR), and many infrared (IR) wavelengths. Previous conceptual models, devices, and methods have typically used laser diodes emitting light having a wavelength of about 810 nm to cut or damage the hair. Light having a wavelength about 600 nm is advantageously not absorbed by blood or not absorbed by blood to a large extent, which helps reduce the risk of adverse effects to the patient, as light having a wavelength above about 600 nm is not absorbed by hemoglobin. Some previous devices and methods have attempted to use flash lamps as a light source; however, these have often been impractical for coupling the light into a delivery system.

However, lighter hair, for example, white and blonde hair, has little or no melanin; therefore, previous devices and techniques attempted to cut light hair by targeting water or keratin. Hair normally contains about 12% water. In some cases, when there is no melanin or an insufficient amount of melanin, NIR and/or IR light can be used and absorbed by water to attempt to cut or damage hair. However, when targeting water, if the fluence of the light is not initially sufficient, the water evaporates from the hair shaft and therefore cannot be used in a second attempt to cut or damage the hair shaft. Surprisingly, white light with or without UV light can damage or cut light, for example, white or blonde, hair.

In some embodiments, devices and methods of the present disclosure use one or more of purple (about 400 nm or in the range of about 380 nm to about 480 nm), blue, and/or blue-green light having wavelengths in the range of about 380 nm to about 500 nm or about 400 nm to about 500 nm to damage or cut hair. In some embodiments, light having a wavelength of about 3000 nm is used to damage or cut hair. Surprisingly, light in these ranges is capable of damaging or cutting light hair, for example, even white and blonde hair. These wavelengths can be selected to target previously unknown chromophores, for example, sebum from the hair follicle. In some embodiments, the wavelengths are selected to target one or more fatty acid(s), phytoshingosine, ceramide, cholesterol, cholesterol sulfate, and/or cholesterol oleate. In some embodiments, the light is selected to target a fatty layer of the hair, on an outer surface of the hair, in the hair, and/or between keratin flakes of the hair. In some embodiments, a user can apply an extrogen chromophore to the hair, the shaving device, or both prior to shaving with any of the devices or according to any of the methods described herein. The extrogen chromophore can be selected to target any desired wavelength(s). These chromophores can advantageously exhibit greater absorption at these wavelengths that previously known chromophores. Additionally, hair typically contains air between layers of keratin. The air pockets can scatter light directed at the hair and increasingly scatter the light as wavelength decreases. Increased scattering lengthens the path of the light in the hair shaft, which increases the probability of the light being absorbed by the hair shaft. The shorter wavelengths in the blue and blue-green range can therefore also cause more scattering, which increases the path length and probability of absorption.

In some embodiments, a shaving device according to the present disclosure can include a single side firing waveguide, such as a laser fiber optic, housed in or supported by a mechanical support. In other embodiments, the shaving device includes more than one fiber. Additionally, in some embodiments, light can be emitted from an end of the waveguide or fiber instead of or in addition to a side.

An example embodiment of a laser shaver 100 is shown in FIG. 1. The shaver 100 includes a handle 102 and a support 140 that supports an optical waveguide, for example, an optical fiber 104, coupled to and extending from the handle 102.

The waveguide can be a fiber, a hollow light guide, a liquid light guide, or any other light guide. For example, in some embodiments, the waveguide 104 is formed from plastic, glass, and/or crystal. The waveguide 104 may include a portion that is cylindrical, tapered along its length, tapered along its width, formed as a wedge, and/or have a rectangular cross section along its length and/or width. Non-limiting examples of such embodiments are illustrated in FIGS. 1C-1G. In some embodiments, the waveguide 104 includes a trunk waveguide and a side-firing waveguide.

The handle 102 generally includes a power source 108, at least one light source 110, for example, a diode laser along with any laser driver boards needed, and one or more optics 112.

In some embodiments, the light source can be or include a Xenon flash lamp. The light source can be configured to emit various wavelengths of light, for example, between about 2500 nm to about 3500 nm, for example, about 3000 nm, or between about 400 nm to about 500 nm. In some embodiments, the light source can be configured to emit UVA light, UVB light, light that is at least about 20% UVA, light that is at least about 20% in the 400 nm to 500 nm range, light that is at least about 20% in the 2700 nm-3500 nm range, light that is at least about 20% in the 3000 nm range, light that includes UVA light, light that includes light in the range of 380 nm to 480 nm range, light that includes light in the 400 nm to 500 nm range, light that includes light in the 2700 nm to 3500 nm range, light that is substantially in the 400 nm to 500 nm range, light that is substantially in the 2700 nm to 3500 nm range, and/or light that is substantially about 3000 nm or about 3000 nm±500 nm in wavelength.

Figure 6:
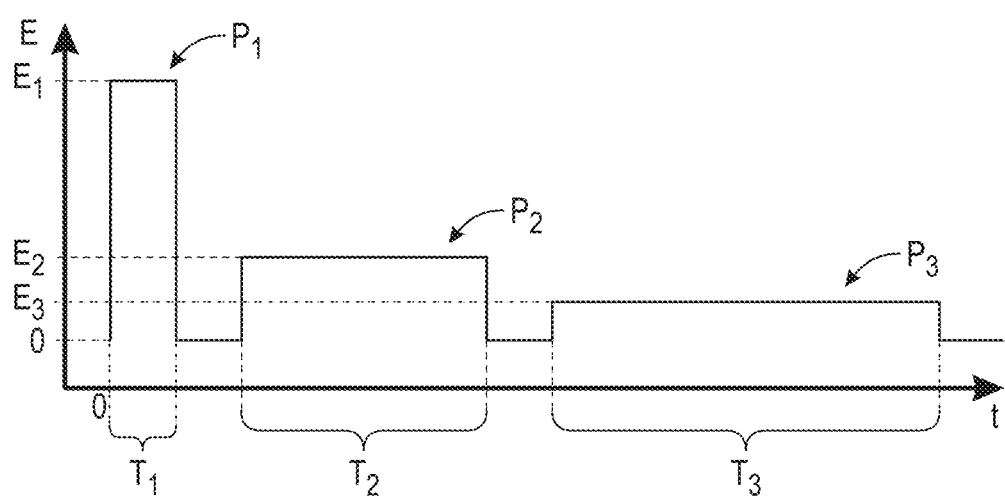
FIG. 6 illustrates one example of a multi-level pulse timing diagram.

The light from the light source 110 may be emitted as a continuous wave or pulsed. In some embodiments, the light is pulsed at a constant rate and at a constant amplitude. In some embodiments, the light is pulsed at multiple, variable amplitudes. One embodiment of a multi-level pulse is illustrated in FIG. 6. In the embodiment of FIG. 6, the light pulse includes three different pulses, P1, P2, and P3. Each pulse has a different amplitude, or energy level, during three consecutive time periods. For example, the light is pulsed at a first energy level E1 during a first time period T1, a second energy level E2 during a second time period T2, and a third energy level E3 during a third time period T3. After the third time period T3, the light pulse pattern repeats.

In other embodiments, only two energy levels and time periods are provided, and in other embodiments, more than three energy levels and time periods are provided. In the embodiment of FIG. 6, a resting time extends between the first time period T1 and the second time period T2, between the second time period T2 and the third time period T3, and between the third time period T3 and the repeated first time period T1. The resting times can be the same duration as each other, different durations, or omitted from the pulse sequence.

In some embodiments, light sources of different wavelengths can be used with a single fiber 104. In some embodiments, light sources of different wavelengths can be coupled into multiple fibers or other light guides. In some embodiments, two or more wavelengths of light may be provided and used to cut the user's hair (or otherwise remove matter). The two or more wavelengths of light may be provided by one or more light sources 110. In one embodiment, a first light source 110 is used to provide a first wavelength of light and a second light source 110 is used to provide a second wavelength of light. In other embodiments, a single light source 110 provides first and second wavelengths of light.

The power source 108 is electrically coupled to the light source 110 to power the light source 110. In use, the light source 110 emits light, which is directed to the one or more optics 112. The one or more optics 112 are configured to couple the light from the light source 110 into the proximal end 104a of the fiber 104. The one or more optics 112 can be a lens or lens system or one or more reflectors. In some embodiments, a separate optic is not necessary, and light can be coupled into the waveguide by proximity or direct or indirect contact. In any embodiment according to the present disclosure, the light can be laser light, coherent light, and/or at least one part of non-collimated light.

Part or all of the shaver 100 can be waterproof or water resistant. In some embodiments, the light source 110 can be located outside the handle 102, for example in a base unit. The base unit can be electrically and/or optically connected to the handle 102 by an electrical conductor or a light conductor. For example, a fiber or umbilicus can transfer the light from the base unit to the handle 102.

In some embodiments, the waveguide or fiber 104 includes a trunk waveguide or fiber and a side-firing waveguide. Light from the light source 100 is carried from the trunk waveguide or fiber to the side-firing waveguide. The side-firing waveguide can include a cutting region 106 for cutting the user's hair. Examples of side-firing waveguides are illustrated in FIGS. 1C-1G. In some embodiments, a single waveguide 104 is provided, and the side-firing waveguide is formed as part of the waveguide 104.

Figure 1B:
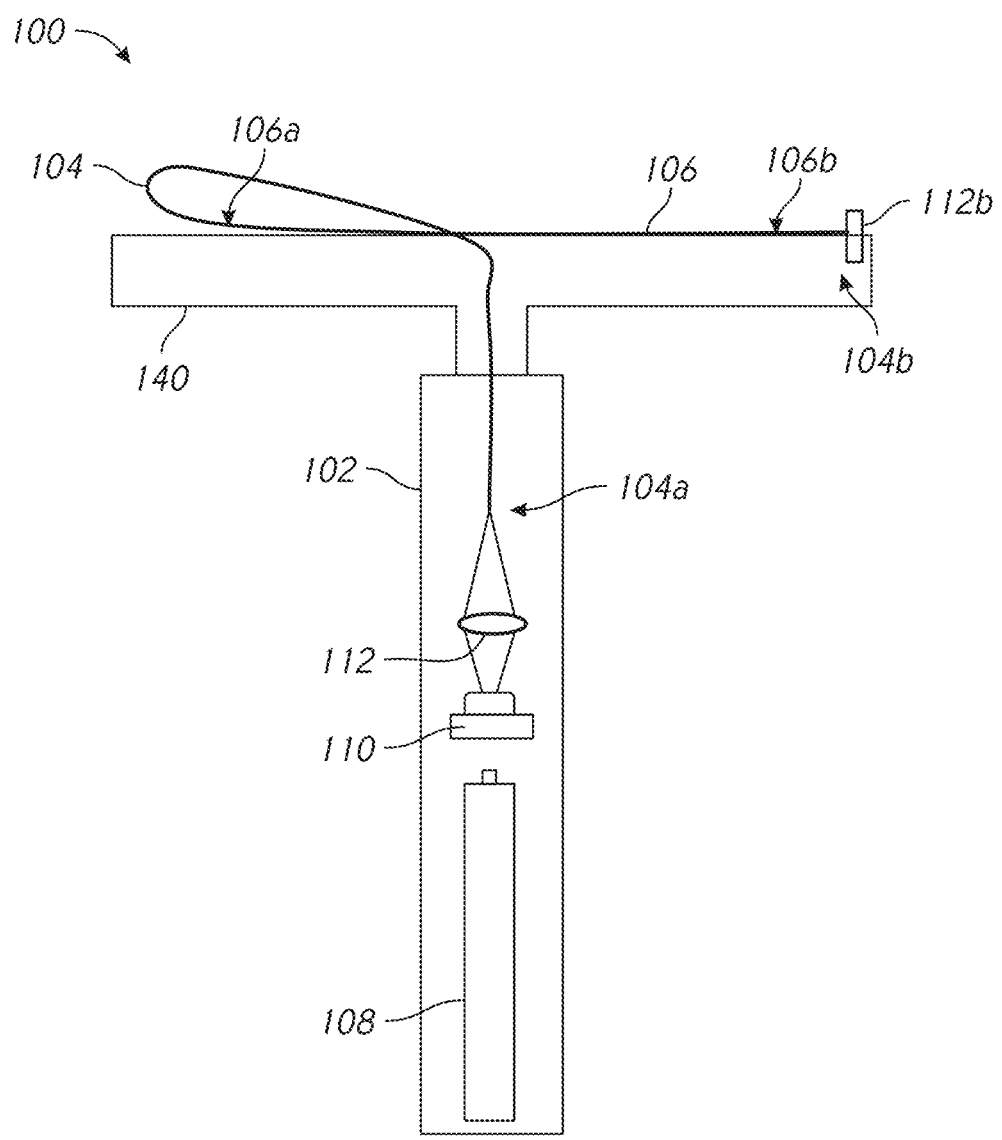
FIG. 1B illustrates another example embodiment of a laser shaving device.
Figure 1C:
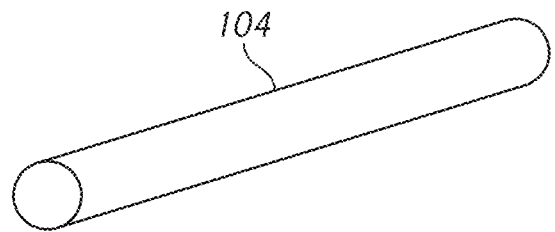
FIGS. 1C-1G illustrate example embodiments of a waveguide suitable for use with any of the laser shaving devices described herein.
Figure 1D:
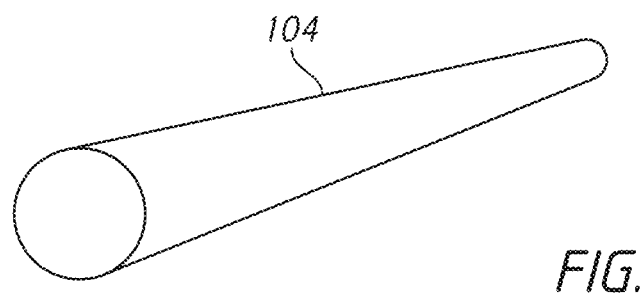
Figure 1E:
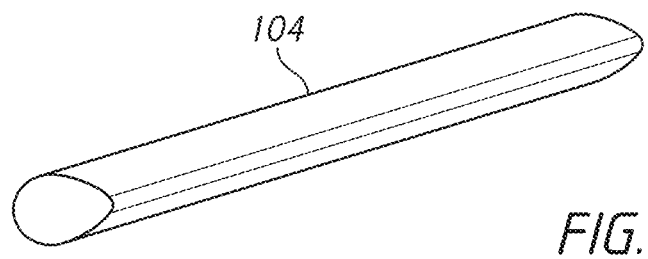
Figure 1F:
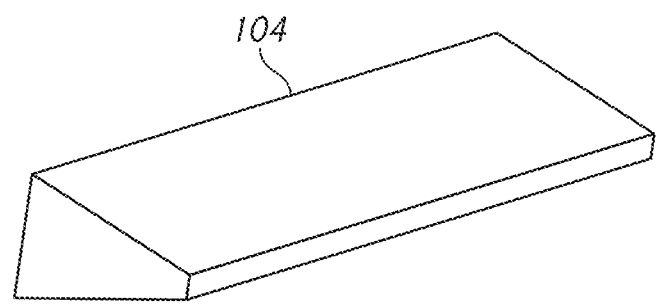
Figure 1G:
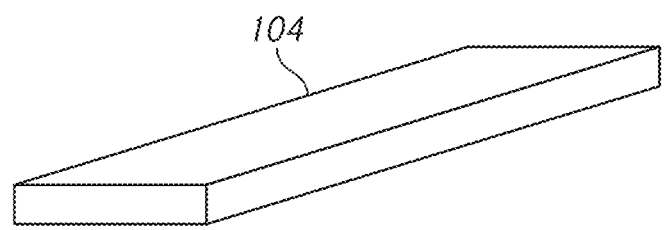

In some embodiments, the optic 112 is and/or includes a mirror that transmits light received from the light source 100 into the fiber 104. The laser shaver 100 can include a second optic 112b (as shown in FIG. 1B) positioned at the distal end of the fiber 104b. The second optic 112b may be located within the support 140, and the distal end of the fiber 104b may bend at the distal end 104b such that the distal end 104b is also located within the support 140 (as shown in FIGS. 1H and 1I). The second optic 112b reflects light from the fiber distal end 104b toward the fiber proximal end 104a. Such reflected light is further reflected by the optic 112 at the fiber proximal end 104a toward the fiber distal end 104b. In such embodiments, it may be advantageous to utilize a fiber 104 that has a gain characteristic (e.g., a fiber laser, etc.), such that the reflected light is amplified by the fiber 104.

For example, the fiber 104 may include a fiber laser, or other material having a gain to increase the optical energy as the laser light is reflected back and forth from distal end 104b to proximal end 104a and back to distal end 104b. Such fibers include fibers that are doped with a gain material such as, but not limited to one or more of: erbium, ytterbium, neodymium, dysprosium, praseodymium, and/or thulium.

In such embodiments, the fiber cutting region 106 is located between the fiber proximal end 104a and the fiber distal end 104b. The fiber cutting region 106 can extend to the distal end 104b of the fiber. In some embodiments, the fiber cutting region 106 does not extend to the distal end 104b of the fiber. In such embodiments, the fiber 104 can include cladding material around the fiber core from the proximal end 104a of the fiber 104 to the proximal end 106a of the cutting region 106, and from the distal end 106b of the cutting region 106 to the distal end 104b of the fiber 104. An unclad (or partially unclad) portion of fiber 104 may be positioned between two clad portions of fiber 104.

Light energy provided by the light source 110 can bounce back and forth between optics 112, 112b within the fiber 104 as the fiber cutting region 106 is brought into contact with hair. The energy stored in the fiber can reach a steady state in about 10-100 ns and the stored energy is released into the user's hair as the cutting region 106 is brought into contact with the user's hair.

Figure 4:
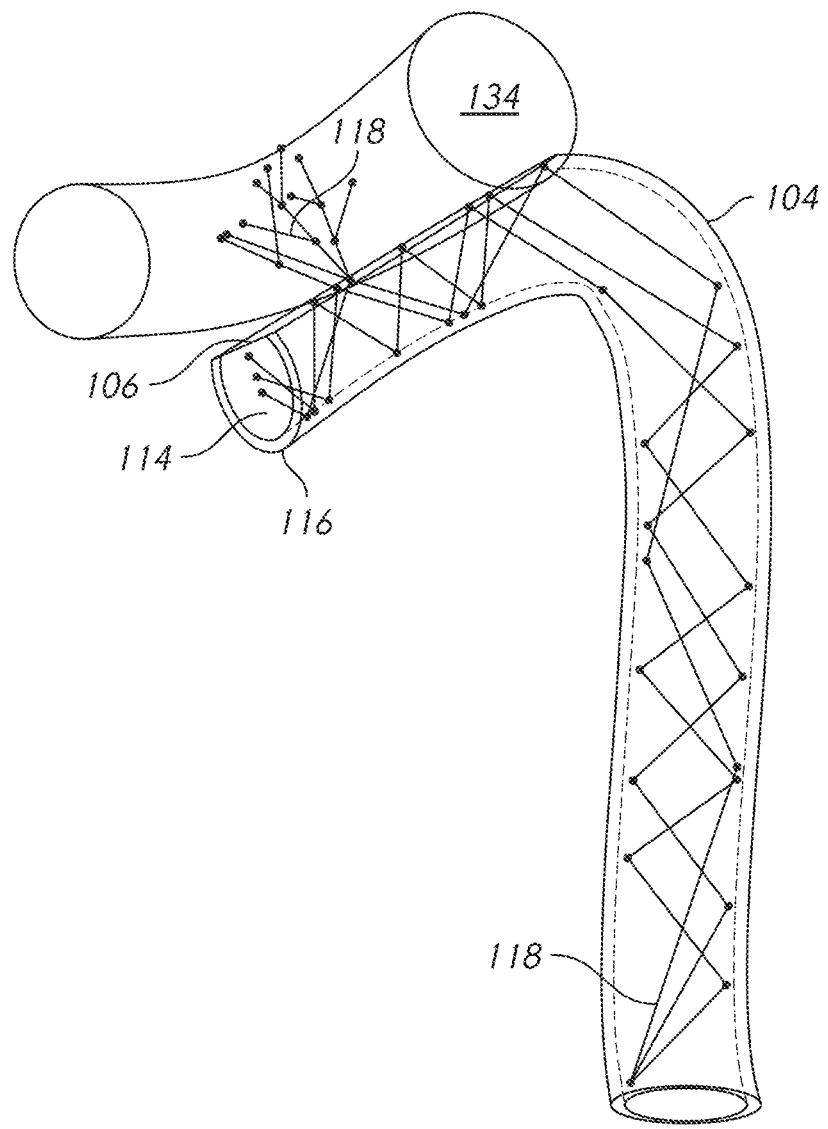
FIG. 4 illustrates a fiber portion of a laser shaver coupling light into a hair shaft.

FIG. 4 illustrates a partial view of the fiber 104. The fiber 104 can have various cross-sectional shapes, for example, round as shown in the illustrated embodiment. As shown, the fiber 104 includes a core 114 and an outer cladding 116 surrounding the core 114. In some embodiments, the fiber core 114 has a diameter in the range of about 4 microns to about 1000 microns. In some embodiments, the fiber core 114 has a diameter between 0.5 mm and 2 mm. In use, light rays 118 propagate along the fiber 104 from the proximal end 104a toward the distal end 104b. The light rays 118 are confined within the core 114 due to the core's higher index of refraction compared to the lower index of refraction of the cladding 116. The fiber 104 includes an aperture or a cutting or light-emitting surface 106 at or near the distal end 104b of the fiber 104. The cutting surface 106 can be shaped to a line having a length of between about 2 mm and about 200 mm. In some embodiments, the cutting surface 106 includes a plurality of optical waveguides or fibers. For example, a single fiber 104 coupled to the handle 102 can couple to a plurality of fibers. In other embodiments, a plurality of fibers or other waveguides can extend from the handle 102. In some embodiments, the cutting surface 106 is positioned along the length of the fiber optic 104, and spaced from the fiber optic's distal end 104b. For example, the entire cutting surface 106 can be spaced a distance from the fiber optic's distal end 104b. The fiber optic 104 may be configured such that the cutting surface 106 does not extend to the fiber's distal end 104b.

Figure 8:
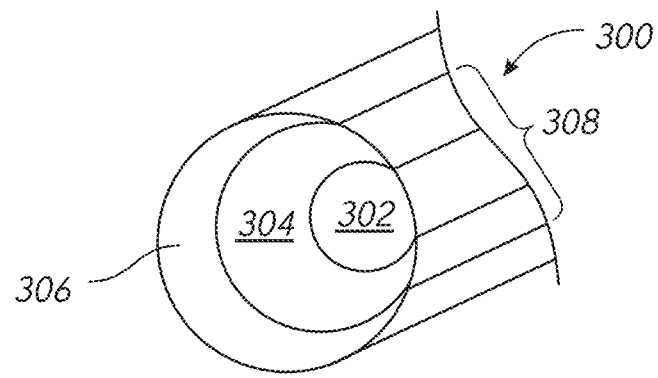
FIG. 8 illustrates one embodiment of a dual core waveguide suitable for use with any of the laser shaving devices described herein.

In some embodiments, different wavelengths of light may be selected to target different chromophores. In addition, in some embodiments, a shorter wavelength of light can be delivered by a smaller waveguide or fiber 104, and a longer wavelength of light can be delivered by a larger waveguide or fiber 104. A dual core waveguide 300 can be designed and/or used to deliver two wavelengths of light. The two wavelengths of light may be delivered simultaneously, or in sequence. One embodiment of a dual core waveguide 300 is illustrated in FIG. 8. The dual core waveguide 300 includes an inner core portion 302. The first wavelength of light is conducted through the inner core portion 302 of the dual core waveguide 300. An outer core portion 304 at least partially surrounds the inner core portion 302. The second wavelength of light is conducted through the outer core portion 304 of the dual core waveguide 300. A cladding portion 306 partially surrounds the outer core portion 304 of the dual core waveguide 300 to expose a cutting region 308 of the dual core waveguide 300. At other, non-cutting region portions of the dual core waveguide, the cladding portion 306 surrounds both the inner core portion 302 and the outer core portion 304 of the dual core waveguide 300. In some embodiments, the outer core portion 304 is an inner cladding portion 304 such that the waveguide 300 is a dual cladding waveguide 300. For example, the waveguide 300 includes a core portion 302, an inner cladding portion 304, and an outer cladding portion 306.

In some embodiments, a light coupling material may be provided to facilitate optical energy coupling from the fiber 104 to the user's hair. For example, the light coupling material may include one or more of a gel, cream, foam, liquid, oil, lipid, glycerol, glycerin, etc. The light coupling material can include an index matching material, such as a material that has an index of refraction that is approximately the same as the index of refraction of hair. In some embodiments, such index matching material has an index of refraction less than the index of refraction of the fiber core 114, but greater than the index of refraction of hair. In other embodiments, the index matching material has an index of refraction greater than that of the fiber core 114 and hair, greater than the fiber core 114 but less than hair, or the same or about the same as hair. The light coupling material can provide increased optical coupling between the fiber 104 and the hair by increasing the surface area of the light-conducting contact region between the fiber 104 and the hair shaft 134. The light coupling material may be applied to the user's skin and/or hair prior to or during use of the shaver 100.

Figure 5:
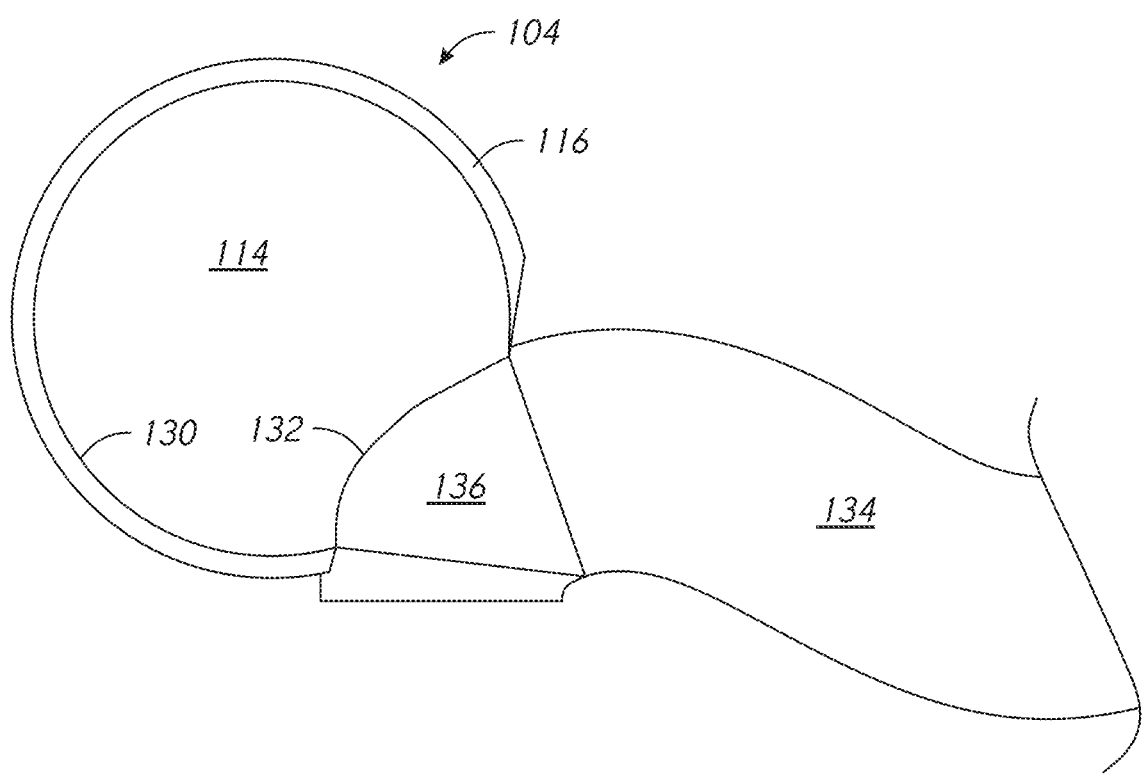
FIG. 5 illustrates a cross-sectional view of another embodiment of a fiber at its cutting region

FIG. 5 illustrates a cross-sectional view of another embodiment of a fiber 104 at its cutting region. The fiber 104 includes a core 114 and an outer cladding 116 that partially surrounds the core 114. The outer surface 130 of the core 114 includes a contoured portion 132. In the illustrated embodiment, the contoured portion 132 is concave, although in other embodiments, the contoured portion 132 can be convex, planar, pointed, wedge-shaped, etc. The fiber 104 and the cutting region can be formed by drawing, extruding, casting, or equivalent technique. The curvature of the contoured portion 132 can provide a lensing effect to assist in directing light out of the side of the fiber 104 and into the hair shaft 134 by forming an optical focusing region 136 within the hair shaft 134. The contoured portion 132 may be shaped to conform to the hair's outside radius and focus energy inside the hair shaft 134 while bending the hair shaft 134.

In some embodiments, the contoured portion 132 is covered at least partially with a coating. For example, a portion of the cladding 116 may be removed from at least a portion of the fiber 104 to expose a portion of the core 114, e.g., on a side of the fiber along its length, and the exposed portion may subsequently be covered by a coating. The coating may be referred to as a "re-cladding." The coating may include any of the coating described above, including but not limited to a clear resin, an organic grease, silicone, petroleum gel, clear PTFE, clear ePTFE, clear rubber, clear RTV, etc. In some embodiments, the coating may be reflective, transmitting, non-reflective, lubricous, and/or configured to grab onto hair. The coating, in such embodiments, may be provided on a cutting surface 106 of the fiber 104. The coating can help protect the fiber from mechanical damage. For example, in some embodiments, the coating provides scratch protection. The coating can include one or more of sapphire, aluminum oxide, silicon oxi-nitride, silicon nitride, diamond (e.g., chemical vapor deposition diamond, etc.), and/or a polymer, such as PTFE, ePTFE, etc., or any other coating material described herein.

In some embodiments, the fiber 104 can include a mirror or fiber re-circulator (not shown) at or near a distal end 104b to reflect the light traveling within the fiber 104 to increase light output and efficiency. The mirror can return and help direct at least part of any non-consumed light to the cutting surface 106. In some embodiments, one or more optical reflective coatings are applied to at least part of the fiber 104 to help recycle radiation within the fiber 104 and improve efficiency.

In some embodiments, the shaver 100 also includes a vacuum (not shown), with an optional filter, positioned near or alongside the fiber 104. The vacuum can be configured to remove smoke that may result from burning the hair.

Figure 2:
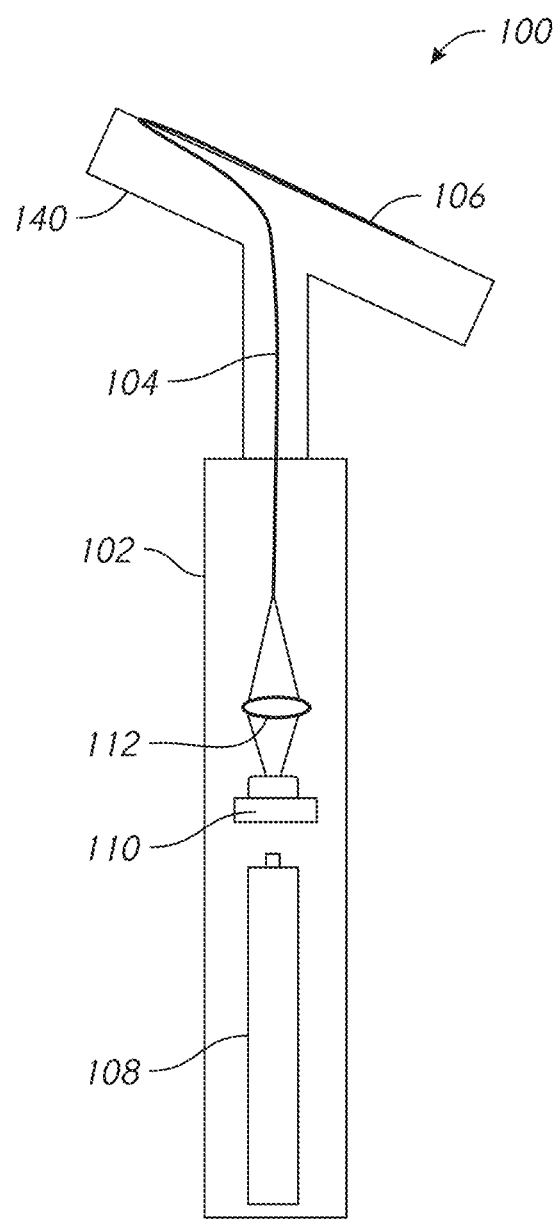
FIG. 2 illustrates another example embodiment of a laser shaving device.
Figure 3:
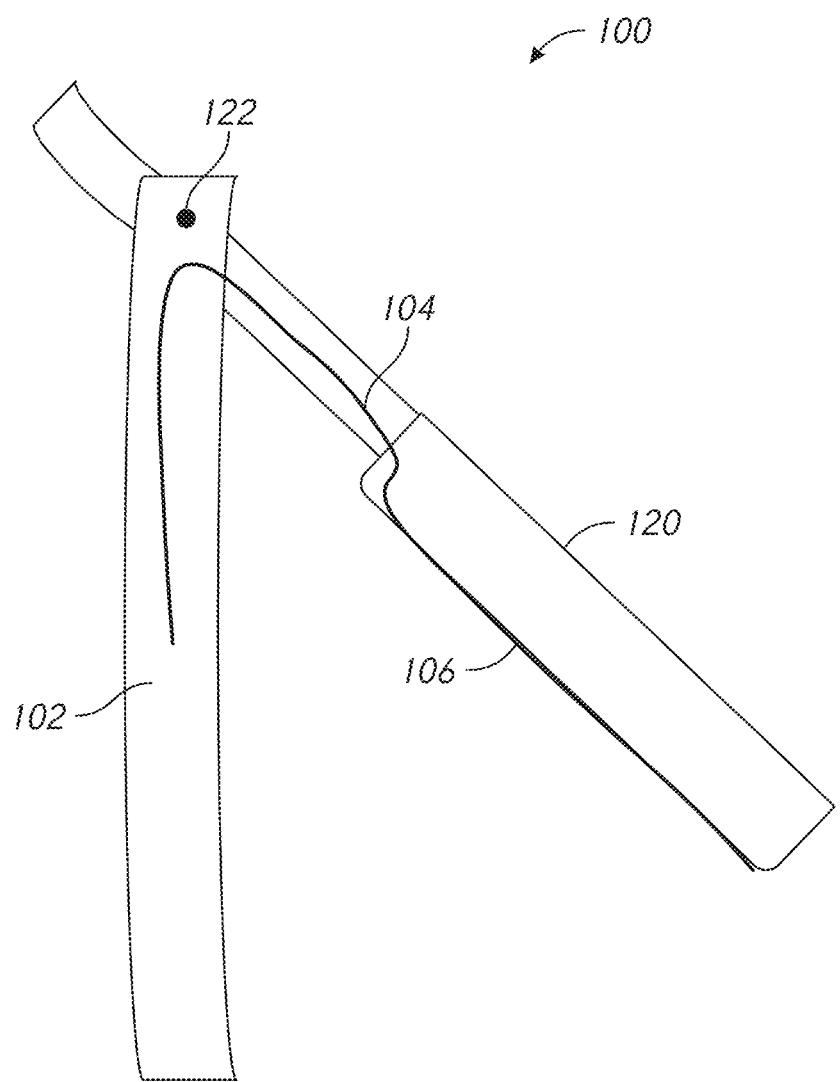
FIG. 3 illustrates another example embodiment of a laser shaving device resembling a straight razor.

The shaver 100 can have various configurations, for example as shown in FIGS. 1-3. The embodiments of FIGS. 1 and 2 have substantially the same handle 102 configuration. However, the fibers 104 and/or supports 140 of the embodiments of FIGS. 1 and 2 have different shapes or configurations. The fiber 104 and/or support 140 can have various shapes and configurations to improve ease of use of the shaver 100. For example, the fiber 104 and/or support 140 can be substantially linear, curved, or include both linear and curved segments. The fiber 104 and/or support 140 can be L shaped, S shaped, T-shaped, or any other suitable shape. In some embodiments, the fiber 104 is held or at least partially contained by a mechanical support 140. A mechanical support 140 provides greater strength and structure to the shaver 100 as a single fiber 104 alone could be too flexible to maintain a desired shape and could be more vulnerable to damage.

In some embodiments, the shaver 100 can be configured to resemble a traditional bladed razor. In the embodiment of FIG. 3, the shaver 100 is similar to a straight razor. In the illustrated embodiment, the shaver 100 includes a support segment 120 that resembles the blade of a straight razor. The support segment 120 is coupled to the handle 102 via a hinge or pivot 122. In some embodiments, the support segment 120 is pivotally coupled to the handle 102 so that the shaver 100 is foldable. The cutting surface 106 of the fiber 104 can be positioned along an edge of the support segment 120 so that the user can use the shaver 100 in a similar manner as he or she would use a straight razor. In other embodiments, the shaver 100 can resemble a safety razor, and the cutting surface 106 can be positioned where a blade would be in a traditional safety razor. In some embodiments, the hinge or pivot 122 is omitted.

Figure 9:
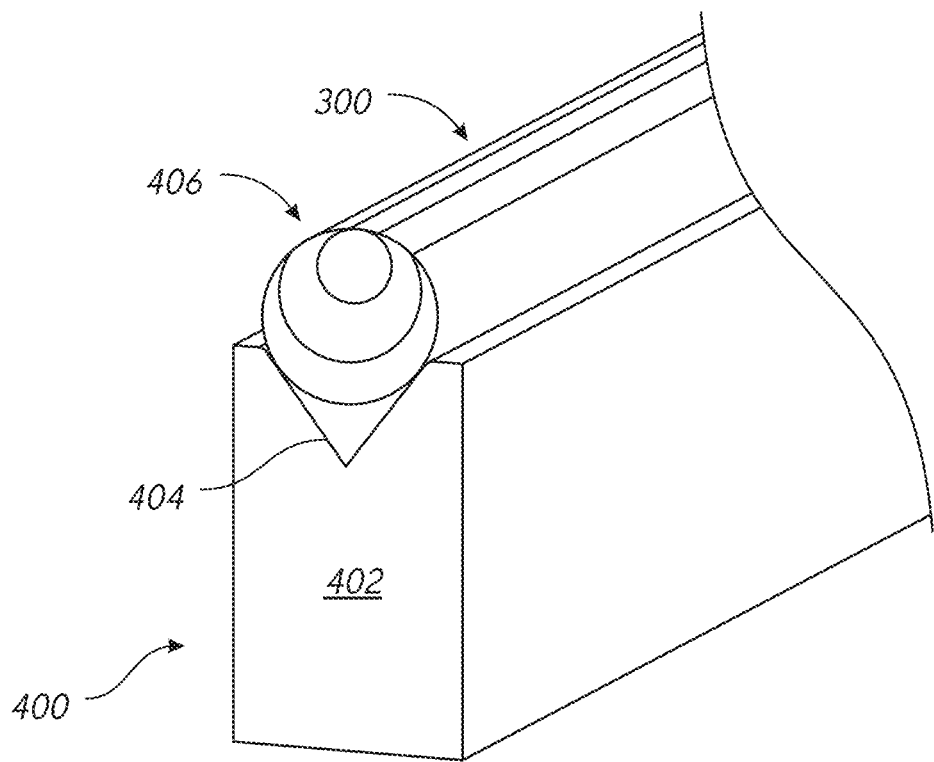
FIG. 9 illustrates one embodiment of a waveguide blade portion suitable for use with any of the laser shaving devices described herein.

In some embodiments, the shaver 100 includes a blade portion 400. The blade portion may be integrally formed with the laser shaver, or may be a removable component. One embodiment of a blade portion 400 is illustrated in FIG. 9. The blade portion 400 includes a support 402. The support 402 includes a waveguide support region 404. In some embodiments, the waveguide support region 404 is a channel formed within a wall of the support 402. The waveguide support region 404 can be a machined edge of the support 402. In some embodiments, the waveguide support region 404 can be machined into the support 402 mechanically or by chemical etching. A fiber or waveguide 406 is supported by the waveguide support region 404. The waveguide 406 can include any of the fibers or waveguides described above, including but not limited to dual core waveguide 300. In the embodiment of FIG. 9, the waveguide 406 includes the dual core waveguide 300 described with respect to FIG. 8.

The support 402, or any support according to the present disclosure, including support 140, can be made of a material that thermally matches the coefficient of thermal expansion of the waveguide or fiber 406 (or any other waveguide or fiber according to the present disclosure, such as fiber 104). For example, the support 402, 140 can be made from a material that has 0.1 to 10 times the coefficient of thermal expansion of the material of the waveguide 406, 104. The support 402, 140 can be made of, but is not limited to, silicon, germanium, aluminum oxide ceramic, aluminum nitride ceramic, silicon carbide, tungsten, and/or steel.

In any of the embodiments shown and described herein, and/or in any embodiment of a shaver 100 according to the present disclosure, the waveguide can be attached to the support by any of a variety of methods, including, but not limited to: glass frit and sintering, anodic bonding, diffusion bonding, soldering with intermediate metal deposition, or by direct deposition or growth of layers of a waveguide. Such a waveguide can be optically clear, having different indices on the portion of the waveguide that is contacting the support 402, 140.

In some embodiments, the shaver 100 is disposable. In other embodiments, the handle 102 is reusable, and the fiber 104 portion including the mechanical support 140 are disposable, similar to a safety razor having disposable cartridges. The fiber 104 portion can be removably coupled to the handle 102 and can be replaced after a number of uses. The proximal end 104a of the fiber 104 can include a connector configured to couple to a connector on the handle 102. One or both of the connectors can be waterproof or water resistant. In some embodiments, an intermediate waveguide can couple a disposable fiber 104 portion to the handle 102.

Figure 7A:
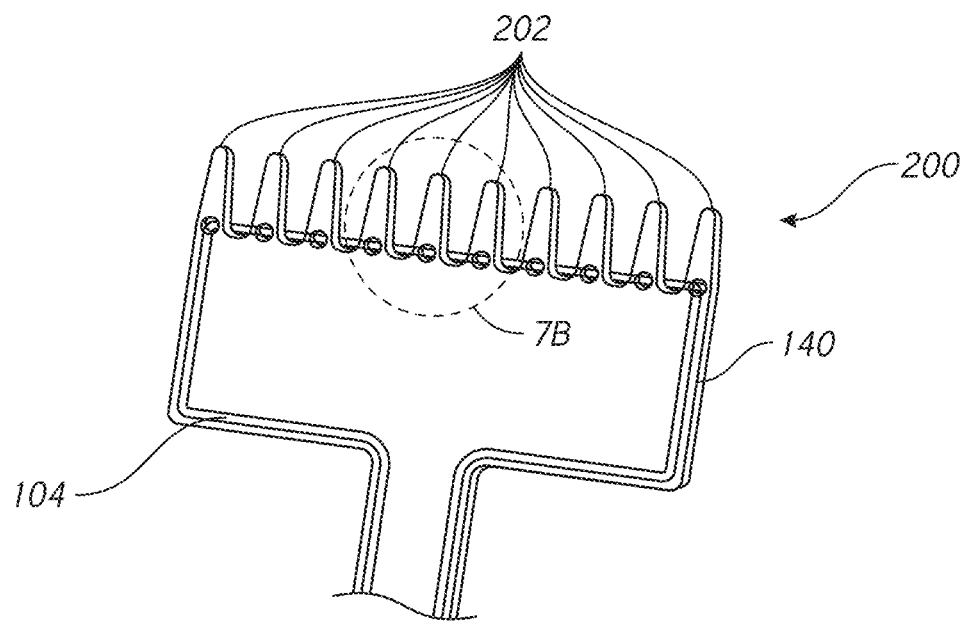
FIGS. 7A and 7B illustrate a comb portion of a support of a laser shaving device.
Figure 7B:
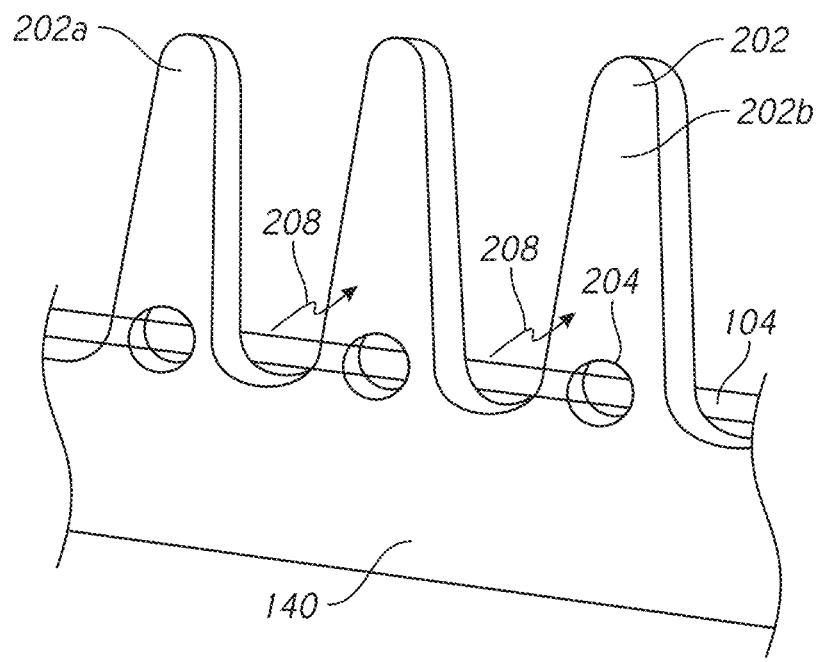

In some embodiments, the shaver 100 includes a comb portion 200 coupled to the support 140. One such embodiment is illustrated in FIG. 7A. The comb portion 200 includes tines 202 that extend from a surface of the support 140. The fiber 104 can extend through openings or around the tines 202. FIG. 7B illustrates a view of a portion of one embodiment of a comb portion 200. The comb portion 200 includes tines 202, and a fiber 104 extends through openings 204 in the tines 202. The fiber 104 may be tapered along its length such that the diameter of the fiber 104 is larger at a first tine 202a than it is at a second tine 202b. The comb portion 200 blocks leaked light 208 that that leaks out of the fiber and that is not directed to the user's hair. The comb portion 202 can also be used to comb through the user's hair (e.g., hair, moustache, beard, sideburns, etc.) during use. The comb portion also protects the fiber 104 by limiting the amount of pressure that the user may exert on the fiber 104 while shaving. Such protection can further prevent the fiber from breaking during use.

In some embodiments, the cutting surface 106 includes a portion of the fiber 104 where the cladding 116 has been removed, for example as shown in FIG. 4. The cladding 116 can be removed via various methods, for example, chemical and/or mechanical methods. Because air and/or water (which may at least partially surround the portion of the fiber 104 with the cladding 116 removed when the shaver 100 is used either dry or wet) has a lower index of refraction than the core 114, the light rays 118 are still confined within the fiber 104. The cutting surface 106 of the shaver 100 must therefore be in contact with hair 134, which has a higher index of refraction than the core 114, for light to be able to couple out of the fiber 104. For example, a fiber 104 having a silica core can have an index of refraction of about 1.47, whereas hair, which is made mostly of keratin with lipids, typically has an index of refraction of about 1.56. In other words, little to no light leaks out of or is emitted from the fiber 104 when the cutting surface 106 is not in contact with the hair or another object having a higher index of refraction than the core. This advantageously confines the laser radiation for safety reasons, for example, for eye safety, and improves the efficiency of the device as the light emitted is used for cutting hair rather than losing light to the room. When the cutting surface 106 is placed into contact with hair 134, the hair shaft begins to draw the radiation from the fiber 104, for example, via evanescent transfer of radiation from the fiber 104 to the hair shaft 134. In some embodiments, the cladding 116 is only removed from a portion of the circumference of the fiber 104 as shown in FIG. 4. This advantageously reduces the risk of a user accidentally contacting another portion of the body with a light emitting portion of the fiber 104. In some embodiments, the shaver 100 can include a sensor configured to detect contact with hair and the shaver 100 can be configured such that the light source 110 is only turned on or active when the cutting surface 106 is determined to be in contact with hair. In some embodiments, the shaver 100 can be configured such that if the shaver 100 is turned on, the light source 110 is turned on but in an idle or low power mode (e.g., 1%, 2%, 5%, 10%, 25%, 50%, etc. of full or cutting power) when not in contact with hair. When the cutting surface 106 is determined to be in contact with hair, the power of the light source can be increased. Such a configuration can allow the shaver 100 to detect contact with hair.

In some embodiments, light is coupled out of the fiber 104 at the cutting surface 106 by using a coating or coupling material, instead of or in addition to removal of the cladding 116. In some such embodiments, the cutting surface 106 does not have to be in contact with hair to emit light. For example, the cutting surface 106 can be processed with photolithography or etching to create a surface that allows light to exit the fiber 104. In some embodiments, a scattering material can be coupled, e.g., glued or adhered, to the cutting surface 106. In some embodiments, both the cladding 116 is removed from the cutting surface 106 and the cutting surface 106 is further processed or a scattering material is coupled to the cutting surface 106. In some embodiments, one or more coatings are applied to at least part of the fiber 104 to enhance energy transfer to the hair shaft. Such coating may optionally be applied to the hair as well (or instead of applying such materials to the fiber 104). Any of a variety of coating or coupling materials may be used, including but not limited to, any of the chromophores discussed herein, petroleum gel, a resin, silicone, room-temperature vulcanization silicone (RTV), polytetrafluoroethylene (PTFE), expanded polytetrafluoroethylene (ePTFE), etc. In some embodiments, the fiber 104 or cutting surface 106 is shaped to optimize radiation transfer to the hair. For example, a distal portion of the fiber 104 can be tapered to change the angles of light being propagated within the fiber until at least some of the light couples out of the fiber 104.

In some embodiments, the shaver 100 includes at least one light front cross-section shaping optic that at least partially arranges coherent light along a line of between about 2 mm and about 200 mm. In some such embodiments, the light passes directly from the light shaping optic to the hair. In other embodiments, the light passes through at least one more optic to be directed to the hair. In some embodiments, the light shaping optic is a waveguide or fiber that at least partially changes the shape of light emitted to a line having a length of between about 2 mm and about 200 mm. In some embodiments, light from the light source is coupled into at least one blade shaped optic that guides at least part of the light to the hair. The blade shaped optic can be a light guide and/or a light transmitter. The blade shaped optic can be detachable, consumable, and/or exchangeable.

For eye safety and/or skin comfort and/or safety, the light is preferably not emitted directly toward the hair, face, or other body parts. In some embodiments, the shaving device is configured to direct the light emitted in a direction parallel or substantially parallel to the skin surface or at an angle selected such that the light does not substantially enter the skin and/or eyes. For example, the shaver 100 and cutting surface 106 can be configured such that light incident on the hair is aimed toward the hair at an angle in the range of about ±45°, for example, in the range of about ±5°, ±10°, or ±25°, to the surface of the skin. In some embodiments, the shaver 100 includes at least one sensor configured to detect a broken fiber. For example, a sensor can be positioned at or near the distal end 104b of the fiber 104 and can detect the amount of light incident on the sensor. If little or no light is reaching the sensor at the distal end 104b, the fiber 104 may be broken and allowing radiation to leak out, which can create a safety hazard. Therefore, if the sensor detects little or no light reaching the distal end 104b, the shaver 100 can turn off the light or power source.

When cutting white (or light) hair with blue light, e.g., at about 403 nm, approximately twice the fluence (or energy level) is needed compared to cutting brown hair (for example, by targeting melanin). Increasing the power can therefore improve the efficacy of the devices and methods described herein in some cases; however, increasing the power can also increase the risk of adverse effects in some cases. In some embodiments, a shaving device as described herein includes one or more sensors configured to detect or gather data indicative of the chromophore(s) present in the target hair. For example, upon contact with the hair, the device can emit light into the hair, and a sensor can detect the light reflected to allow the device to determine the wavelengths of light absorbed. In some embodiments, the sensor could be located in the handle of the device. In some embodiments, the sensor can be a MEMS device that functions as a spectrometer and is located on the portion of the device configured to emit light to and/or contact the hair. If the sensor detects and/or the device determines based on sensor data that the hair contains a sufficient amount of melanin, the device can reduce the energy level or power and/or adjust the wavelength of light emitted to target a predetermined chromophore (e.g., melanin). If the sensor detects and/or the device determines based on sensor data that the hair lacks sufficient melanin but contains sufficient sebum, the device can increase the energy level or power and/or adjust the wavelength emitted to target the sebum.

Fiber Masking and Coating

In some embodiments, the index of refraction of portions of the waveguide is varied to control light emission. For example, the waveguide can be configured to direct light in a particular, desired direction by tuning or otherwise adjusting the index of refraction of the cutting region and/or contact, side-firing emission waveguide blade and masking regions of the waveguide where emission or contact is undesirable.

In the case of shaving, for instance, it is desirable to bring the waveguide as close as possible to the skin without directing light into the skin. The epidermis of the skin has a higher index of refraction than the dermis, and the epidermis of the skin has a lower index of refraction than hair. For example, the index of refraction of the epidermis of the skin is about 1.477 at around 400 nm and lower at longer wavelengths while the index of refraction of hair is about 1.569 at 400 nm, particularly when the major composition of hair is keratin. In such cases, a waveguide index lower than the hair but higher than the skin will reduce or eliminate light coupling into the skin, while still coupling light into the hair in order to sever or cut the hair. In some embodiments, it is therefore desirable to provide a waveguide having an index of refraction greater than about 1.477 and less than about 1.569, at 400 nm.

In one embodiment, such a waveguide is provided or manufactured by depositing a film of tuned index onto a fused silica substrate or fiber (or other substrate), or by doping the fused silica (or other substrate) with phosphate or germanium dioxide.

In some embodiments, the waveguide may be "masked off" at its cutting region. For example, lithography or shadow mask coatings of highly reflective or absorbing film may be provided in the region where contact of the waveguide with skin is anticipated (the cutting region). In another embodiment, a low index barrier layer coating may be provided as a cladding on only the side of the waveguide that is anticipated to contact the skin (the cutting region). In another embodiment, a fiber index profile is configured in such a way that a cladding layer is drawn during the fiber process.

Thin Film Deposition and Films or Coatings on the Waveguide or Fiber

It can be beneficial to prevent or inhibit cutting debris from diffusing into the waveguide, which could create or contribute to defects, making it brittle and adversely affecting longevity. The process of laser light cutting of organic tissue can also cause or contribute to localized high temperatures and involves debris (including minerals and carbonaceous organic matter) deposits on the surface of the waveguide, which is brought into contact with the material(s) being cut. The high temperatures in combination with the carbonized, aerosolized, deposited debris can drive the debris molecules into the waveguide. Diffusion or introduction of debris molecules into the waveguide can induce structural defects in the bulk of the waveguide. This can make the waveguide brittle and reduce its longevity.

A solution to, or way to improve, avoid, or reduce, this potential problem is to apply a dense optical coating, film, or film stack to at least a portion of the waveguide. Such a coating can serve as at least one of a physical diffusion barrier and an optical thin film. The dense coating can be deposited on the waveguide using, for example, ALD (atomic layer deposition), PVD (physical vapor deposition), CVD (chemical vapor deposition), IBS (Ion beam sputtering), and/or any other technique that can produce a dense film of material, which can prevent or inhibit diffusion of debris into the waveguide. The film can be made of or include metal oxide, metal nitride, carbon, silicon, and/or other dielectric compounds. Other films can be used.

A thin film or coating applied to at least a portion of the waveguide can help solve or improve other potential issues. For example, if one side of a waveguide has a cladding with a higher index than the other side of the waveguide, or if the cladding on one side is completely removed, the modes and the light in the waveguide will be pulled toward the higher index cladding side. This phenomenon is unfavorable to the operation of the on-contact, side emitting waveguide cutting technology described herein because the more light that is concentrated near the side of the waveguide where the contact with the target material is made, the higher the light coupling will be, which can cause or contribute to a faster cutting operation. To combat this issue, a thin film of an optically clear material with a higher index than the waveguide can be deposited on or applied to at least a portion of the waveguide. The film can have an optical index of refraction in the range of 0.5 to 3 times the index of the waveguide.

In some embodiments, the film has a thickness that is on the order of the wavelength of light intended to be used or up to 4 times thinner or thicker than the wavelength of light used (e.g., the dimension of the wavelength inside the film). The thickness of the film, or any one or more layers that make up the film, can be in the range of 5 nm to 10,000 nm. Other thicknesses can be used, as well. The thickness of the film can be adjusted to control or affect coupling of light from the waveguide into the target (e.g., hair or organic tissue). The thickness of the film can have a gradient and/or pattern of thickness variation along a length of the cutting region. Since the index of the layer of material is higher than that of the guiding region (e.g., the main body or core of the waveguide) but the film or layer is thin, it creates an effective index that compensates for the mode pull away from the surface without it. Once the film or layer is deposited, the mode and light concentration in the guiding region will return to a symmetrical (or relatively more symmetrical) profile or favor the cutting surface or region.

Furthermore, in some embodiments, the film or layer thickness is selected to be at odd multiples of ¼ wavelength, weighted by angle and index of refraction. A film having a thickness that is ¼ of the wavelength of light from the light source within the film can dramatically increase the coupling efficiency between the waveguide and the hair. The wavelength of the light within the film can be determined as the free space wavelength (the wavelength of the light in free space) divided by the index of refraction. This can allow the film to produce a characteristic impedance match between the waveguide and the target (e.g., hair or tissue), dramatically increasing the coupling efficiency of the electromagnetic field from the waveguide to the target when the target is brought in contact with the thin film. In order to control the coupling efficiency and/or promote a more uniform distribution of coupling along the waveguide, the thickness of the film can be tuned off of the peak coupling efficiency thickness and/or deposited with a thickness gradient along the length of the waveguide, which can help equalize coupling efficiency as the light leaks or couples out along the length of the blade, e.g., light out-coupling side of the fiber.

The film material can act as an integral component of the waveguide and can advantageously therefore have low defect density and high optical clarity at the wavelength of interest. The deposition techniques mentioned herein can produce the lowest (or reduced) defect density, pinhole free (or with reduced pinholes) thin films which are waveguide quality. Other deposition methods can be used. In some cases, it can be advantageous to deliberately introduce a certain pinhole density in the thin film in order to scatter a small fraction of the light.

The thin films can be patterned on the waveguide surface through, for example, etching or deposition techniques to produce various properties such as hydrophilicity, hydrophobicity, oleophilic, oleophobic, and/or photocatalytic properties, depending on the application involved.

Additionally or alternatively, electrically conductive and/or resistive transparent films, which include but are not limited to indium tin oxide or tin oxide, can be deposited on at least a portion of the waveguide surface. For example, such films may be deposited by deposition methods or they may be diffused into the glass or crystalline surface of the waveguide to produce a thin, transparent, electrically conductive layer.

A strip of electrically conductive and/or resistive (or semi-resistive) coating can also be applied onto the outer, cutting surface of the waveguide, or waveguide blade. Such coating can be used to heat up the waveguide's cutting surface and to maintain the waveguide's cutting surface at a sufficient temperature to enable the natural oils of the skin to flow on the waveguide's cutting surface. In such case, the waveguide's cutting surface becomes oleophilic and forms a uniform film of oils on its cutting surface, thereby improving light coupling into the object to be cut (e.g., hair, etc.).

In some embodiments, a photocatalytic, self-cleaning and/or oleophilic coating is provided on the contact, cutting surface of a waveguide, or waveguide blade.

Photocatalytic Coating

A photocatalytic, self-cleaning coating can be made of photocatalytic material, including but not limited to $TiO_2$ thin film. Such a film may have a thickness of 2 nm to 1000 nm. When the film interacts with light having a wavelength between 300 nm and 500 nm, the film has the ability to break down organic material deposited on the film's surface. The photocatalytic process is powered by the sun and natural humidity in the air and breaks down dirt and organic depositions on the cutting surface, which can then be washed or wiped off.

A material such as $TiO_2$ acts as a wide bandgap semiconductor, which generates hydroxyl radicals on the surface when illuminated by blue or UV light, as well as a super-hydrophilic, water adsorbing surface. Other materials such as $ZrO_2$ and $ZnO$ (primarily metal oxides) have also been reported to possess similar properties. The combination of these properties with light at certain wavelengths begins a combination of reactions that cause a breakdown of organic matter on the surface coated with these films.

The coating is hydrophilic and binds water molecules, which can be dissociated by light in the UV spectrum with the action spectrum tailing off in the violet visible portion of the spectrum. However, the coating still remains effective in the violet region of the light spectrum. The light interaction with water produces hydroxyl radicals, which break down the organic material and dirt, and spread them over the surface or wash them away during operation (e.g., shaving). In some embodiments, a photocatalytic film can help start the process of damaging the hair shaft. This affect can cascade with the incident light to help speed up cutting of the hair shaft. A photocatalytic film can therefore be a reactive film rather than a passive film.

Figure 10:
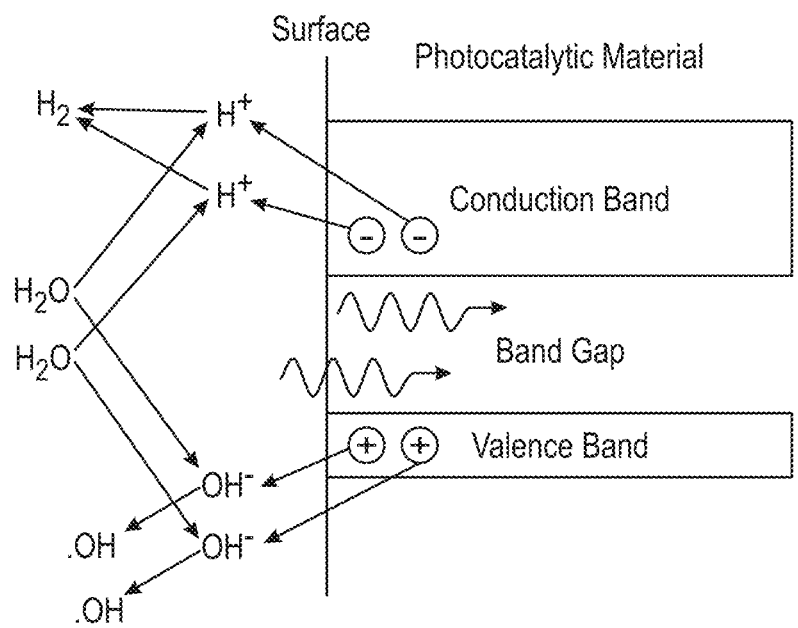
FIG. 10 illustrates a schematic of a photocatalytic process.

Shown in FIG. 10, the first step in the chain of reactions is the electron-hole pair generation in the semiconducting thin film (which is typically in the range of 10's of atomic layers thick) after a photon in the UV-violet region of the spectrum is absorbed in the film. The generated electrons are then taken up by the hydrogen ions that dissociate from the water molecules to produce $H_2$ gas and the holes take up the extra electron of the hydroxide ion produced from the same water molecules producing a hydroxyl radical or a neutral $^-OH$ radical compound, denoted at $^-OH$, which is highly reactive and breaks down organic materials by mineralizing organic compounds and converting them into water soluble matter.

The strongest absorption of $TiO_2$ and photocatalytic compounds in general is in the UV region (150 nm-400 nm). This absorption also extends slightly into the visible region where it is weak but present in the 400 nm-420 nm spectral region. In at least one subsequent work it has been observed that when, at least, $TiO_2$ has implanted Cr or V ions, the absorption shifts to the red direction of the spectrum and begins to absorb up to 540 nm depending on the concentration of the dopant.

When a photocatalytic film is applied to the cutting surface of a contact-cutting, side-firing, emission waveguide blade, internal light in the waveguide scatters out enough light at high intensity onto the small waveguide surface such that it serves as a photo catalyst. The photo catalyst breaks down the material that remains on the surface during cutting. Such remnant materials are then easy to clean off the waveguide (e.g., with a cleaning solution) or they simply evaporate off of the waveguide's cutting surface. In one embodiment, a photocatalytic film is a self-cleaning film configured to dissolve organic compounds when photons excite electron hole pairs near the film surface. In such cases, electron hole pairs combine with water to produce hydroxyl radicals, which help dissolve organics on the film surface. Photocatalytic films can be used to maintain a clean surface (e.g., shaving surface) and disinfect it at the same time. Also such films can be used to initiate the cutting of the hairshaft, which can cascade with incident light and help speed up the hair shaft cutting. A photocatalytic film can be a reactive film rather than a passive film.

When a photocatalytic coating is applied to the waveguide at the interface with air, the photocatalytic process as described above can help breakdown organic materials, thereby assisting in: (1) cleaning and self-cleaning the waveguide surface; (2) tissue or other organic material breakdown for cutting or shaving applications, for example, using a side-cutting, contact-emission waveguide blade; (3) disinfection of cuts and/or surfaces (e.g., skin surfaces) during the cutting process by breaking down pathogens; and/or (4) disinfection of bulk liquids by submerging waveguides in the liquid.

Compared to the standard photocatalytic process, this process is unique because the light that gets absorbed in the photocatalytic thin film because the direction of propagation of the light is along the waveguide axis. In other words, typically photocatalytic coatings require illumination by external light, or light incident on an outside surface. In contrast, photocatalytic coatings according to the present disclosure operate on light propagating internally within the waveguide that includes the photocatalytic outer surface coating. The wave-front is propagating parallel to the axis, i.e. substantially parallel to the surface. When light coupled from the waveguide core and/or an intermediate film on the waveguide into the photocatalytic coating is incident on the photocatalytic coating substantially parallel or at an angle approaching parallel to the surface of the coating, the light has a longer path in the photocatalytic coating and a higher probability of absorption in or by the coating. When the photocatalytic coating is brought into contact with a hair, the light path in or along the photocatalytic coating to couple into the hair becomes more perpendicular, which can result in or allow less loss of surface-emitted and organic tissue cutting light. In some embodiments, the waveguide surface is tapered.

In some embodiments, the waveguide and/or photocatalytic coating can be selectively doped via ion implantation and a selectively patterned mask. The selectively doped waveguide and/or coating can emit light at certain wavelengths from the un-doped regions of the photocatalytic coating and absorb light to put into effect the photocatalytic process in the doped regions, thereby causing or allowing for a dual action of the photocatalytic process combined with light emission.

In some embodiments, the use of multiple wavelengths of light can cause or allow for a dual action of light emission and the photocatalytic process.

In some embodiments, tuning a wavelength to the absorption curve where partial light at any one particular wavelength can be emitted can cause or allow for a dual action of light emission and the photocatalytic process.

In some embodiments, using a wavelength that is >about 99.8% absorbed by the thin film can allow the use of a non-biologically safe wavelength to cause or allow for a mostly photocatalytic process for cutting and disinfecting.

Figure 11:
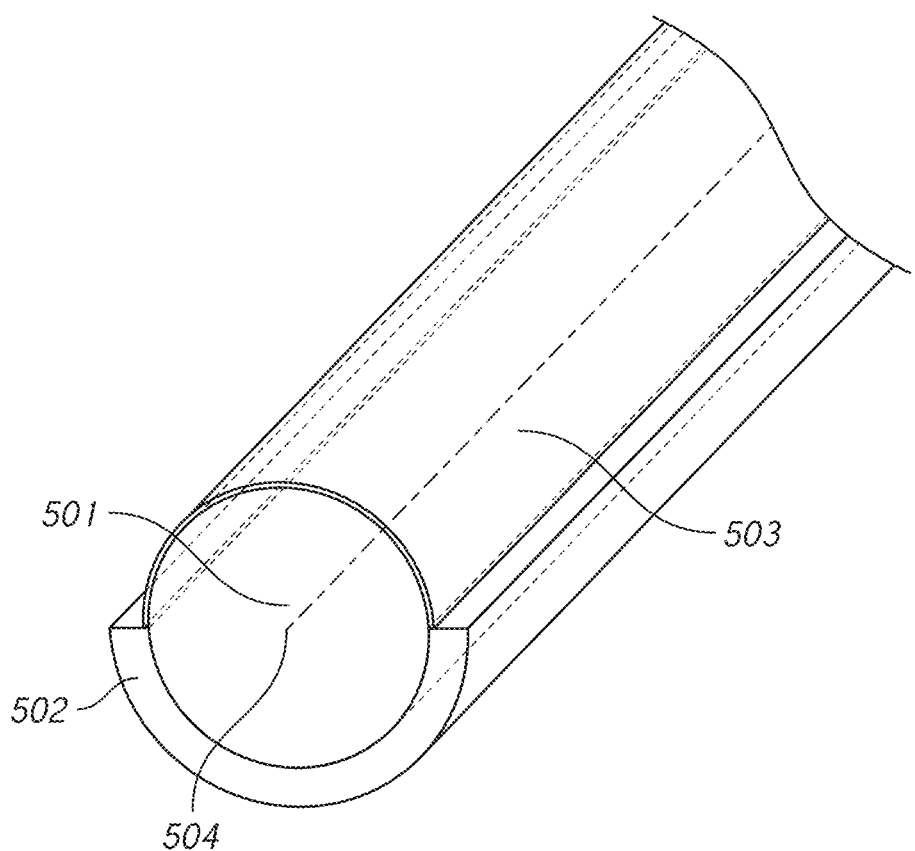
FIG. 11 illustrates a schematic of a waveguide having a photocatalytic coating.
Figure 12:
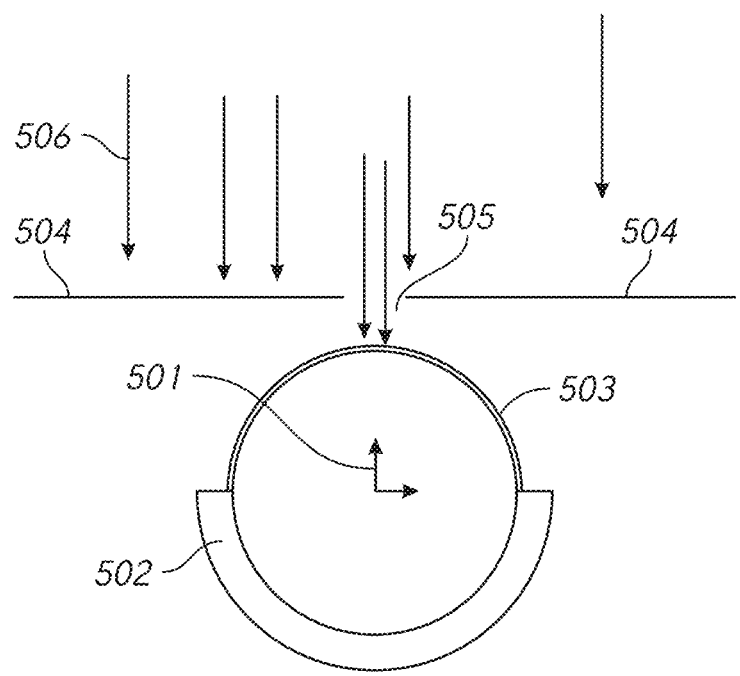
FIG. 12 illustrates a method of creating a photocatalytic coating on a waveguide via ion implantation.
Figure 13:
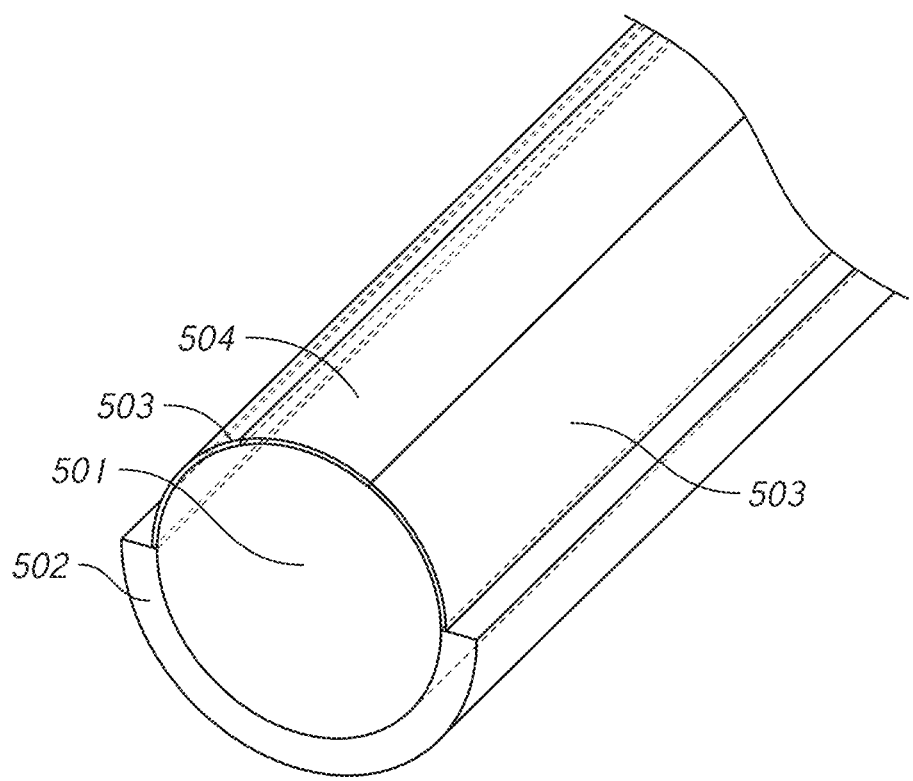
FIG. 13 illustrates a waveguide having a photocatalytic coating formed as shown in FIG. 12.
Figure 14:
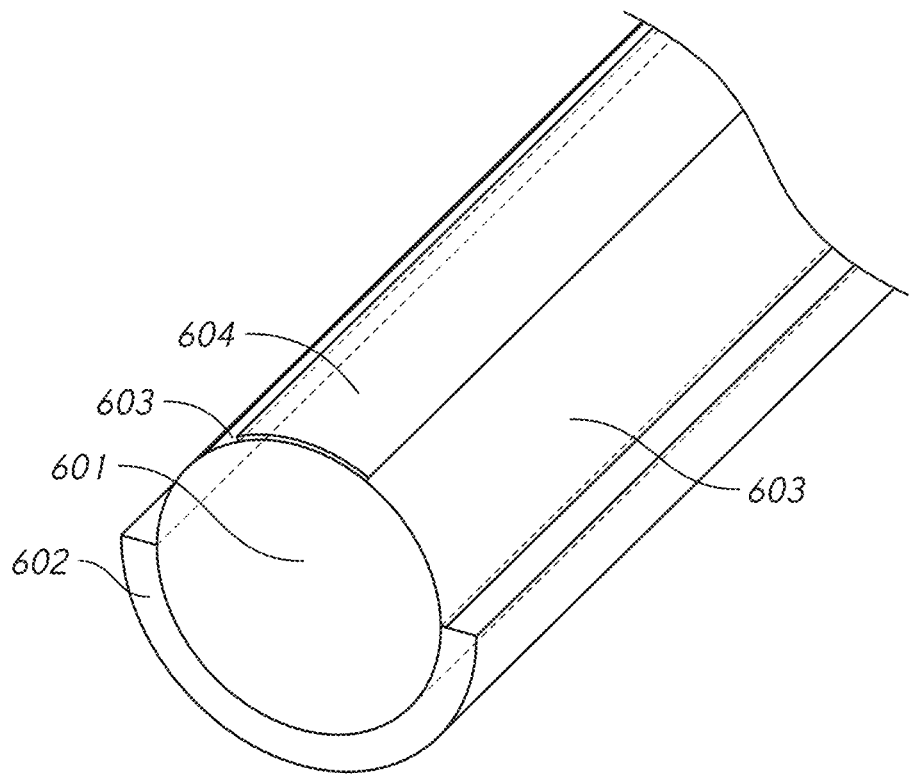
FIG. 14 illustrates a waveguide having a photocatalytic coating formed by wet or plasma etching.

FIGS. 11-14 show a waveguide having a photocatalytic coating at various stages of manufacture. In other words, FIGS. 11-14 show a method of manufacturing a waveguide having a photocatalytic coating. FIG. 11 shows the waveguide with a guiding region or core 501, a cladding 502, a photocatalytic thin film, 503, and the optical axis 504. FIG. 12 shows the waveguide (e.g., a fiber) being irradiated by an ion beam for ion implantation into the thin film, where 501 is the guiding region, 502 is the cladding, 503 is the photocatalytic thin film, 504 is the mask, 505 is an opening in the mask and 506 is the ion beam direction. FIG. 13 shows the film 504 with the ions implanted into a masked region where 501 is the guiding region, 502 is the cladding, 503 is the undoped photocatalytic thin film, 504 is the photocatalytic thin film region doped by ion implantation. Certain light may exit 503 without inducing a photocatalytic process but when the same light is absorbed in 504, it generates a photocatalytic region. FIG. 14 shows another waveguide having a guiding region 601 and cladding 603 in which a photocatalytic region can be produced by either wet or plasma etching. As shown, the thin film was etched off and light can exit from a first region 603, and a non-etched region 604 includes a region of photocatalytic thin film on the contact emission surface.

Intermediate Layer for Improved and/or Selective Coupling into Tissue

When an optical waveguide is brought into close proximity with a target media of higher index (e.g., index of refraction) than air, a certain amount of coupling will occur between the modes in the waveguide and the media. This coupling can be due to evanescent fields and/or simply frustrated total internal reflection. If a thin layer of intermediate material is placed between the waveguide and the target media, the coupling efficiency may be enhanced. The coupling efficiency and/or improvement in the coupling efficiency can depend on or be affected by the thickness of the intermediate material layer with respect to the wavelength used, the indexes of the waveguide and target media, and/or the index of refraction of the intermediate material.

Depending on the relative indexes of refraction of the waveguide and the target material, a thin intermediate layer can impedance match the electromagnetic field from the waveguide to the target media in order to increase or maximize coupling. If the intermediate layer is tuned off the wavelength, then the coupling can be reduced or minimized.

Therefore, for any given wavelength of light used in the waveguide, the intermediate layer thickness and index of refraction can be selected to provide optimum or improved coupling from the index of the waveguide to the index of a certain target. For any given wavelength of light used in the waveguide, the intermediate layer thickness and index of refraction can also or alternatively be selected not to improve or optimize coupling from the index of the waveguide to the index of a different target, thereby creating selective coupling. In some embodiments, the waveguide can be a fiber or a deposited waveguide, and the waveguide and/or an intermediate layer on the waveguide can have a lower index of refraction than the index of refraction of human hair.

The indexes of refraction of the hair are substantially different from those of the dermis and the epidermis, beginning with the outer stratum corneum layer. The epidermis including the stratum corneum has a lower index of refraction than the hair.

If an intermediate layer in the form of a single thin film or a thin film stack with a certain effective index is tuned to impedance match and provide optimum or improved coupling between a certain waveguide index and hair for a predetermined wavelength, it can also be tuned to lower the effective coupling into indexes other than those of the hair's narrow range, making the skin index of refraction outside the coupling region of the tuned waveguide.

This provides a mechanism for a close shave using the side-coupling, optical waveguide blade, shaving technology (for example, shavers 100 as shown and described herein). The cutting surface can be placed in optical contact with the skin and not couple into the skin but instead, selectively couple into the hair in order to melt and sever the hair so that it is level or flush to the skin.

Figure 18:
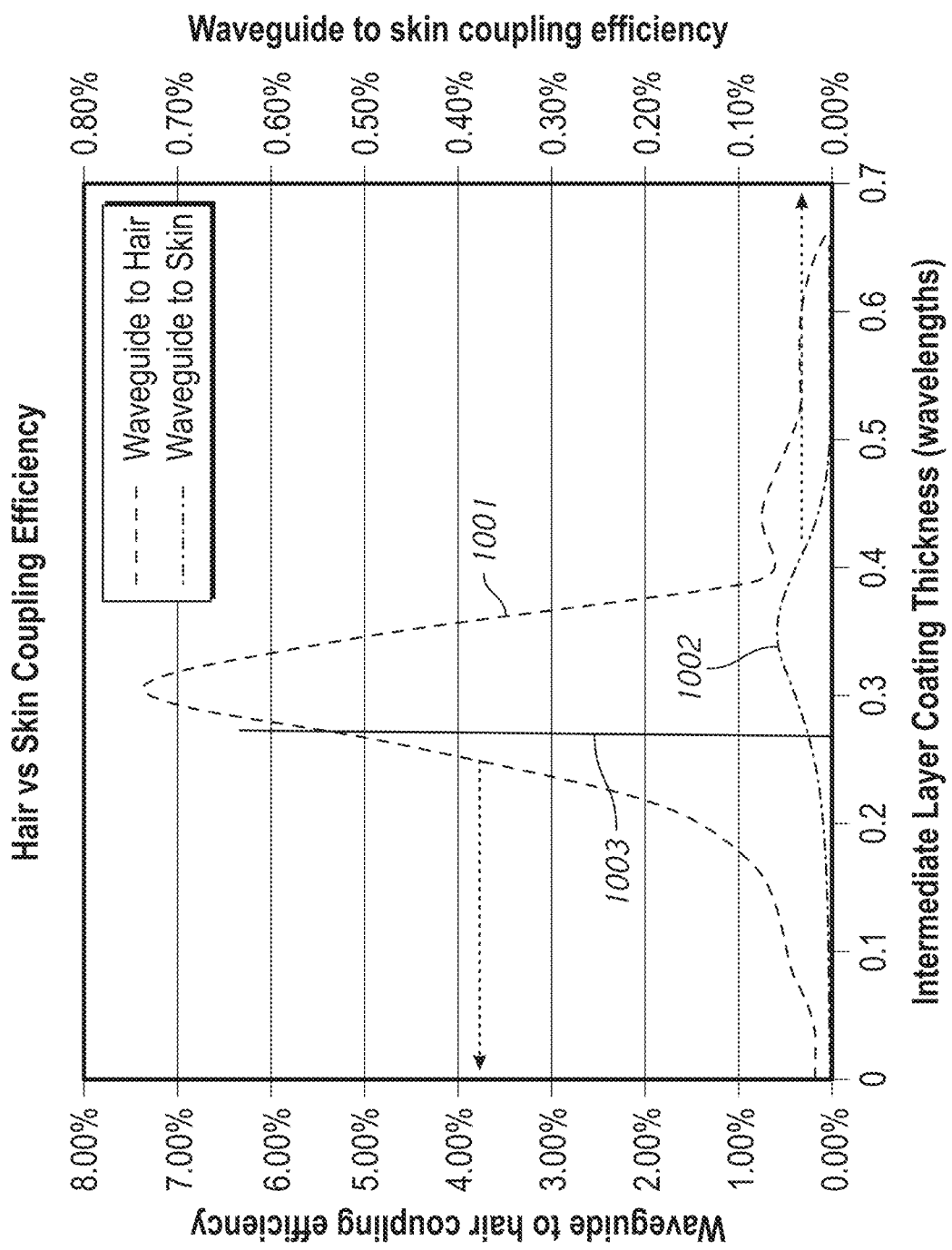
FIG. 18 illustrates a graph showing coupling efficiency as a function of a thickness of an intermediate layer coating on a waveguide.

FIG. 18 shows a simulation of coupling efficiency plots into hair and skin versus intermediate layer thickness in terms of wavelengths. FIG. 18 shows a relationship 1001 of coupling efficiency out of the waveguide into hair as a function of intermediate film thickness, and a relationship 1002 of coupling efficiency out of the waveguide into skin as a function of intermediate layer thickness. The scale of the relationship 1002 is $1/10^{th}$ of the scale for relationship 1001. The line 1003 illustrates one embodiment of a preferred thickness of the film of a certain high intermediate index.

In some embodiments, the thickness of the film is selected to obtain a desired tradeoff between higher absorption into a first material (e.g., hair) and lower absorption into a second material (e.g., skin). For example, the film thickness can be selected to obtain a desired ratio (e.g., a predetermined ratio) or a ratio within a desired range of ratios (e.g., a predetermined range of ratios) of hair absorption to skin absorption. In another embodiment, the film thickness is selected to obtain a hair absorption value within a predetermined distance (e.g., within one standard deviation, within 1.5 standard deviations, within two standard deviations, etc.) from the peak of the hair coupling efficiency curve 1001, and to obtain a skin absorption value within a predetermined distance (e.g., more than one standard deviation, more than 1.5 standard deviations, more than two standard deviations, etc.) from the peak of the skin coupling efficiency curve 1002. In another embodiment, the film thickness is selected to obtain a hair absorption that is at least a predetermined amount (e.g., 10%, 25%, 50%, etc.) of the maximum absorption in hair (corresponding to the peak of the hair coupling efficiency curve 1001), and to obtain a skin absorption value that is no greater than a predetermined amount (e.g., 10%, 25%, 50%, etc.) of the maximum absorption in skin (corresponding to the peak of the skin coupling efficiency curve 1002). In one embodiment, the intermediate layer thickness is selected to be within one standard deviation of the layer thickness corresponding to the peak in the hair coupling efficiency curve 1001 and to be more than 1.5 standard deviations from the layer thickness corresponding to the peak in the skin coupling efficiency curve 1002. In another embodiment, the intermediate layer thickness is selected to be within two standard deviations of the layer thickness corresponding to the peak in the hair coupling efficiency curve 1001 and to be more than two standard deviations from the layer thickness corresponding to the peak in the skin coupling efficiency curve 1002. In another embodiment, the intermediate layer thickness is selected to provide a coupling efficiency into hair of at least 50% of the peak coupling efficiency into hair (the peak coupling efficiency corresponding to the peak in the hair coupling efficiency curve 1001) and to provide a coupling efficiency into skin that is less than 50% of the peak coupling efficiency into skin (the peak coupling efficiency corresponding to the peak in the skin coupling efficiency curve 1002).

In some embodiments, the first material is the skin and the second material is the hair. In such embodiments, the intermediate layer thickness is selected to increase coupling into the skin while reducing coupling into the hair. Such embodiments may be desirable in non-shaving applications where heating the skin is desirable, such as in cauterization, wound treatment, heat therapy, tissue cutting, etc.

In some embodiments, an optical waveguide includes two or more therapeutic regions from which light is emitted out of the waveguide. In some embodiments, each therapeutic region includes an intermediate layer having a different thickness, made of a different material, or both. For example, in one embodiment, a shaving waveguide has a first region where an intermediate layer having a first thickness is provided, and a second region where an intermediate layer having a second thickness is provided. The first thickness is selected to provide coupling efficiency within one standard deviation of the peak coupling efficiency into hair and to provide coupling efficiency that is more than one standard deviation away from the peak coupling efficiency into skin. The first region can correspond to a hair cutting or shaving region of the waveguide. The second thickness is selected to provide coupling efficiency within one standard deviation of the peak coupling efficiency into skin and to provide coupling efficiency that is more than one standard deviation away from the peak coupling efficiency into hair. The second region can correspond to a heating or cauterizing region of the waveguide. In some embodiments, the first and second regions extend along the axial length of the waveguide and are parallel to and circumferentially separated one another. In some embodiments, the first region is proximal (or distal) to the second region along the axial length of the waveguide.

Since the index of refraction of the skin is low to begin with, the coupling efficiency is much lower even at the peak. However, the peaks for coupling into hair and into skin are not aligned. That is because the perturbation of the waveguide is different depending on whether the hair and its higher index are brought into close proximity with the waveguide or the skin and its lower index are brought close to the waveguide. This difference in the peak efficiency locations can be used to an advantage by selecting an intermediate layer thickness or a multilayer stack design in such a way that it (a) lies within about +/−1 standard deviation of the coupling efficiency curve and above the coupling efficiency range from waveguide into hair and (b) lies outside about +/−1.0 or 1.5 or another predetermined number of standard deviations of the coupling efficiency curve for the skin.

In some embodiments, a waveguide can have an intermediate layer or a thin film multi index coating stack on an active region of the waveguide. The thickness and/or index of refraction of the layer, coating, or stack can be selected such that at a predetermined wavelength of set of wavelengths, the active region allows at least 1% of light to couple from the waveguide into hair but allows less than 0.1% of light to couple into skin (e.g., skin around the hair, at the base of the hair, etc.). In some embodiments, the coupling of the light can be controlled for selected modes.

In some embodiments, a method of using a waveguide or fiber as described herein, for example, a waveguide or fiber having an intermediate layer or film on at least a portion of the waveguide or fiber, includes placing the waveguide in contact with skin such that a shaving blade angle of attack that is formed between the blade (waveguide or fiber) and the skin at the base of the hair is such that the cutting region is in firm contact with the skin around, adjacent, or near the base of the hair.

In some embodiments, an intermediate layer, film, or film stack as described herein can be made of or include dielectric materials such as, but not limited to, diamond, $Al_2O_3$, $TiO_2$, or Si.

A similar method can be utilized to design a cutting blade for laser surgery, or any other cutting, affecting, or treating of matter using a fiber blade, where it is desirable to discriminate between tissues having different indices of refraction and to prevent or inhibit accidental and unnecessary or unwanted laceration of organs or other materials, tissue, matter, etc.

Index Profile of Fiber or Waveguide

In some embodiments, the waveguide or fiber is shaped and/or its refractive index profile is shaped to improve out-coupling of light from the waveguide's or fiber's contact surface.

An index profile of the waveguide or fiber can be adjusted to optimize coupling. In one embodiment, a fiber has an annular outer core that surrounds an inner core. The outer core has a higher index of refraction than the inner core. The index difference will cause energy within the fiber to move toward the perimeter of the guiding volume. In one embodiment, to transfer energy from the fiber waveguide to the object to be cut (e.g., hair, etc.) an annular or semi-annular index profile with a low index in the center of the core is provided. A concentric, higher index annulus or semi-annulus is provided on the side of the intended emission. A low index cladding is provided on the side opposite to that of the emitting interactive surface. In some embodiments, no cladding is provided, or it is only provided around a portion of the outer core. Such configuration allows the optical modes to push out from the center of the core to the edge of the core and it suppresses modes that are less useful. Less useful modes are suppressed because light energy traveling in lower order modes does not contact the walls of the core effectively enough to transfer energy to the object in contact with the fiber walls (e.g., hair, etc.). This can be accomplished by one or more of: (1) coating the fiber (e.g., on its cutting surface) with a film having an index of refraction higher than the waveguide, (2) drawing a fiber with a desired index profile preform that puts higher index outer core around a low index core, or (3) implantation or diffusion of ions into the exposed interactive surface of the waveguide to increase the index of refraction close to the surface of the guiding region.

The area where the fiber will be coupling light to the hair (e.g., the cutting surface) can have an optimized cross sectional shape that has more affinity to oils, moisture, etc. to assist in the cutting process.

In some embodiments, the fiber is corrugated in order to scatter lower order modes into a higher order in a multimode fiber. The higher order modes will propagate their energy closer to the wall of the waveguide. A corrugated backing for the waveguide, which forces the waveguide to be undulated, will also serve to scatter lower order modes into higher order modes, thus facilitating fiber-to-hair optical coupling, as well. In some embodiments, an undulated waveguide will have regions of convex orientation with respect to the cladding side. By increasing the angle of incidence of radiation close to the critical angle will couple radiation out more easily into the hair in those regions.

Laser Knife

In some embodiments, a waveguide, for example, a waveguide including one or more features as described herein, can be incorporated or formed into a knife. The knife can be used to cut organic and/or inorganic materials using laser radiation. When the waveguide contacts the object to be cut, the contact frustrates the total internal reflection of laser radiation contained in the waveguide and couples laser radiation from the waveguide into the object being cut. Upon removing the object from the waveguide blade, the laser radiation is still contained in the waveguide.

This laser knife can be used for surgical techniques as well as household applications, including kitchen applications, woodworking, agricultural work, and yard work, industrial cutting, any applicable professional cutting including, for example, electronics applications such as insulation removal, among other applications.

Figure 15:
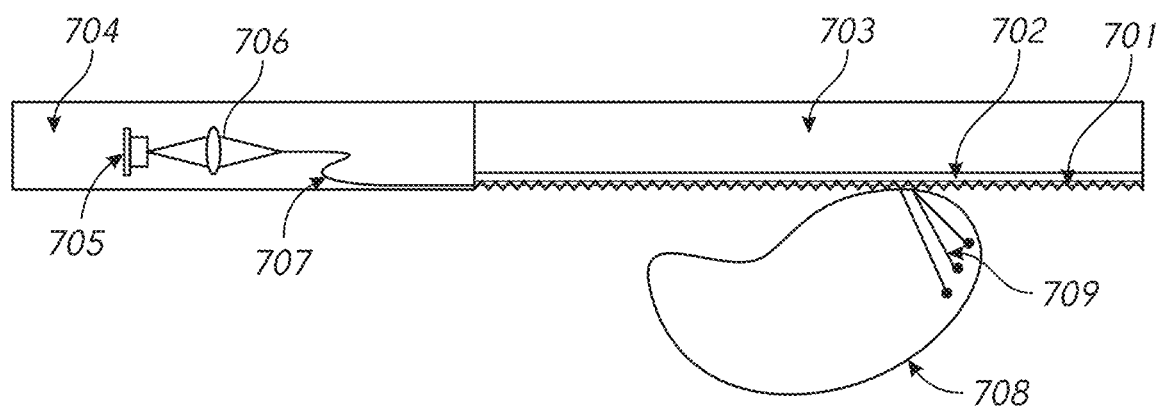
FIG. 15 illustrates an example embodiment of a laser knife.

One embodiment of a laser knife in the form of a straight blade (e.g. the support structure 703 is in the form of a straight blade) is shown in FIG. 15. The waveguide 701, which guides the light by total internal reflection, can be an optical fiber or other waveguide with at least one part of the waveguide's side accessible for cutting the object 708 to be cut. Cladding 702 contains the light and prevents or inhibits its leakage into the support structure 703. The laser knife can include a handle 704 or another structure that contains the laser engine 705 and coupling optics 706. A fiber 707 guides the light into the final waveguide 701. As shown, rays 709 emitted from the blade or waveguide 701 are absorbed into the object 708 and converted into heat and/or ablation energy needed to dissociate bonds of the object 708.

Figure 16:
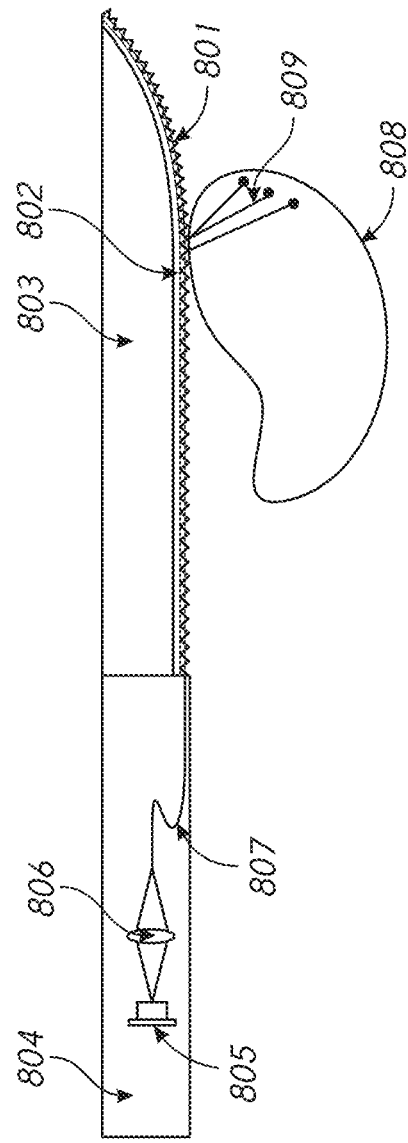
FIG. 16 illustrates another example embodiment of a laser knife.

Another embodiment of a laser knife having a blade (e.g., support structure 303) with a straight portion and a curved portion is shown in FIG. 16. The waveguide 801, which guides light by total internal reflection, can be an optical fiber or other waveguide having at least one portion of its side accessible for cutting the object 808 to be cut. Cladding 802 contains the light and prevents or inhibits its leakage into the support structure 803. The laser knife can include a handle 804 or another structure that contains the laser engine 805 and coupling optics 806. A fiber 807 guides the light into the final waveguide 801. As shown, rays 809 emitted from the blade or waveguide 801 are absorbed into the object 808 and converted into heat and/or ablation energy needed to dissociate bonds of the object 808. In the embodiment of FIG. 16, the curvature of the curved portion facilitates light leakage into the object 808. Light that exceeds the critical angle in the curved portion of the waveguide 801 can exit the waveguide 801 and initiate a cut or a damage in the object 808 to be cut, which can facilitate further cutting with the straight portion.

Figure 17:
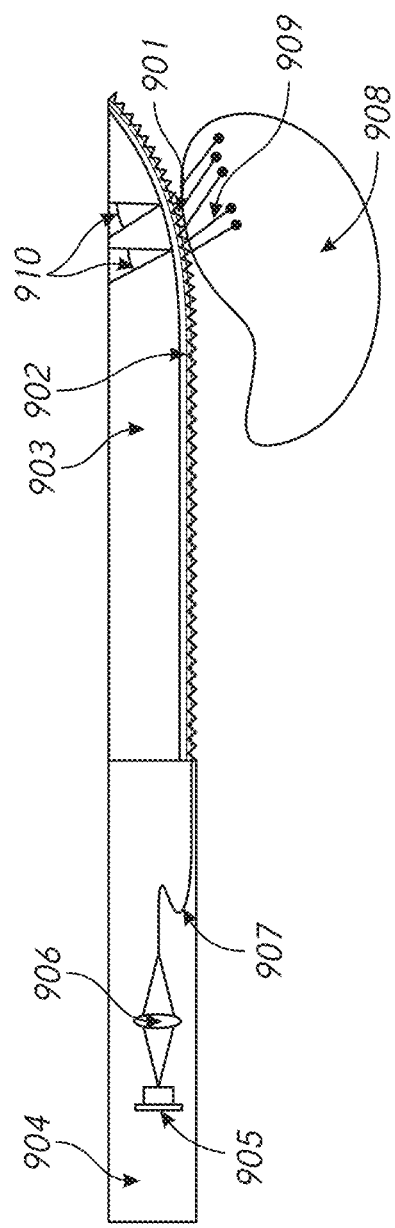
FIG. 17 illustrates another example embodiment of a laser knife.

FIG. 17 illustrates another embodiment of a laser knife having a blade (support structure 903) that has a variable self-adjusting curvature. The waveguide 901, which guides light by total internal reflection, can be an optical fiber or other waveguide having at least one portion of its side accessible for cutting the object 908 to be cut. Cladding 902 contains the light and prevents or inhibits its leakage into the support structure 903. The laser knife can include a handle 904 or another structure that contains the laser engine 905 and coupling optics 906. A fiber 907 guides the light into the final waveguide 901. As shown, rays 909 emitted from the blade or waveguide 901 are absorbed into the object 908 and converted into heat and/or ablation energy needed to dissociate bonds of the object 908. During use of the laser knife of FIG. 17, when pressure is applied to the knife during cutting, the curvature of the blade increases, and the increased curvature increases or promotes coupling of light from the waveguide into the object 908 due to the increase of the angles of incidence inside the waveguide 901. As the object material is removed (e.g., melted or ablated off) (or the blade is removed from the object 808), pressure is decreased and the blade curvature is reduced to release more light because spring flexures 910 in the support structure 903 compress during application of pressure and relax to straighten out the waveguide after cutting begins thereby straightening out the waveguide 901. This makes the device self-adjusting.

Terminology

More than one device as described herein can be used synchronously or in sequence to cut or damage hair.

Although the devices and methods herein have been described with respect to cutting or damaging hair, these devices and methods can be used for other applications, for example, surgery. The device or cutting surface 106 can be shaped similar to a knife, surgical scalpel, or other cutting tool. In some embodiments, when using the device to cut tissue, the device can also act as a coagulating and bleeding stopping means by means of the heat created by light absorbed into the tissue. The light can be modulated and tuned to cut tissue or coagulate. The devices and methods herein can also be used to cut other organic material, such as plant matter, grass, leaves, flowers, etc. In one embodiment, a laser shaver 100 is configured for cutting a lawn or trimming a hedge.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A device configured to cut hair using laser light, the device comprising:
    a shaving portion configured to be coupled to a handle portion, the shaving portion comprising:
        a support;
        a waveguide supported by the, the waveguide having a first end, a second end, an outer side wall, and a cutting region positioned towards the second end and extending along a portion of the outer side wall;
        wherein the shaving portion is configured to provide laser light having a wavelength selected to target a chromophore to cut a hair shaft,
        wherein the waveguide is positioned to receive laser light at the first end, conduct the laser light from the first end toward the second end, and emit at least a portion of the laser light out of the cutting region and toward hair, and
        wherein the cutting region of the waveguide is configured to have a refractive index that is greater than the refractive index of skin.

2. The device of claim 1, wherein the refractive index of the waveguide is less than or equal to the refractive index of hair.

3. The device of claim 1, wherein the waveguide further comprises a coating or a film.

4. The device of claim 3, wherein the coating or film comprises a thin film or a tuned index film or film stack.

5. The device according to claim 3, wherein the coating or film comprises one or more of metal oxide, metal nitride, carbon, silicon, sapphire, aluminum oxide, silicon oxi-nitride, silicon nitride, diamond, a chemical vapor deposition, an atomic layer deposition, a physical vapor deposition, an ion beam sputtering, diamond, a polymer, polytetrafluoroethylene (PTFE), expanded polytetrafluoroethylene (ePTFE), plastic, glass, crystal, a dielectric compound, a deposition or growth; and/or,
    electrically conductive, electrically resistive, transparent, indium tin oxide, tin oxide, oleophilic, oleophobic, hydrophilic, hydrophobic, self-cleaning, and/or photocatalytic; and/or,
    wherein the coating comprises a photocatalytic film comprising $TiO_2$, optionally wherein the photocatalytic film has a thickness in the range of from 2 nm to 1000 nm.

6. The device according to claim 1, wherein the coating or film has an index of refraction greater than about 1.477 or less than about 1.569 at 400 nm, or wherein the refractive index of the waveguide at the cutting region is greater than 1.47 or 1.477, or wherein the refractive index of the skin is lower than 1.477 at wavelengths longer than 400 nm, or wherein a refractive index of the hair is about 1.56 or 1.569.

7. The device according to claim 1 wherein the coating or film has an optical index of refraction in the range of 0.5 to 3 times the index of refraction of the waveguide.

8. The device according to claim 1, further comprising a coating,
wherein the coating is applied to only one side of the waveguide along its outer side wall; and/or,
wherein the coating comprises a film having a thickness in the range of 5 nm to 10,000 nm, on the order of a wavelength of the laser light or up to four times thinner or thicker than the wavelength of the laser light; and/or,
wherein the coating comprises a film having a thickness that is an odd multiple of one-quarter of a wavelength of the laser light.

9. The device according to claim 1, wherein the waveguide is further configured to prevent light from being emitted from the cutting region when the cutting region is not in contact with the hair.

10. The device according to claim 1, wherein the support or wave guide comprises a bend; and/or,
wherein the support comprises a channel configured to receive the waveguide, and wherein the waveguide is positioned within the channel; and/or,
wherein the waveguide is removably coupled to the support; and/or,
the device further comprises the handle portion, and wherein the shaving portion is configured to be removably coupled to the handle portion.

11. The device according to claim 1, wherein the wavelength is within one or more ranges selected from a group consisting of: 380 nm to 480 nm, 380 nm to 500 nm, 400 nm to 500 nm, 400 nm to 700 nm, 2500 nm to 3500 nm, 2950 nm to 3050 nm, and 2700 nm to 3500 nm; and/or,
wherein the chromophore is selected from the group consisting of: sebum, a fatty acid, phytoshingosine, ceramide, cholesterol, cholesterol sulfate, cholesterol oleate, water, keratin, and melanin.

12. The device according to claim 1, further comprising an optic, the optic configured to direct the laser light toward the first end of the waveguide; and/or,
further comprising a reflector positioned at the second end of the waveguide and configured to reflect at least a portion of the laser light towards the waveguide's first end.

13. The device according to claim 1, wherein the waveguide has a diameter in the range of about 4 microns to about 1000 microns; and/or,
wherein the waveguide comprises a core and a cladding that surrounds the core along the waveguide's length, except at the cutting region; and/or
wherein the waveguide comprises a fiber optic; and/or,
wherein the waveguide is at least partially parallel to the support; and/or
wherein the waveguide comprises plastic, glass, crystal, silica, phosphate, or germanium dioxide.

14. The device according to claim 1, wherein the waveguide has a radius of curvature at the cutting region that is different than a radius of curvature of the waveguide near its first end; and/or,
wherein a cross-sectional shape of the waveguide at its cutting region is wedge-shaped, rectangular, convex, planar, or pointed; and/or,
wherein the waveguide tapers in diameter along its cutting region; and/or
wherein the waveguide comprises a portion that has a rectangular cross section along its length and/or width, or wherein the waveguide comprises a planar waveguide, or wherein the waveguide includes a portion that is tapered along it width and/or length.

15. The device according to claim 1, wherein an index of refraction of the waveguide is less than an index of refraction of the hair shaft; and/or,
wherein the index of refraction of the waveguide is greater than an index of refraction of air.

16. The device according to claim 1, wherein the waveguide comprises a substrate or a substrate of silica.

17. The device of claim 16, further comprising a film of tuned index deposited onto the substrate.

18. The device of claim 1, wherein the index of refraction is higher towards the surface of the cutting region of the waveguide.

19. The device of claim 1, wherein the waveguide comprises a selectively doped waveguide.

20. The device of claim 19, wherein the selectively doped waveguide comprises an ion implantation or a diffusion of ions.

21. The device of claim 1, wherein the waveguide comprises a core and wherein the cutting region is a portion of the outer side wall of the core.

22. The device of claim 1, wherein the waveguide further comprises a core and a cladding, or a re-cladding, or a coating, which surrounds the core, and wherein the cutting region is a portion of an outer side wall of the cladding, the re-cladding, or the coating.

23. The device of claim 1, wherein the cutting region comprises a thin film.

24. The device of claim 1, wherein the waveguide further comprises a core and a cladding that partially surrounds the core, and wherein the cutting region is formed in the side wall of the core.

25. The device of claim 1, further comprising a comb portion coupled to the support.

26. A method of shaving hair with laser light, the method comprising: providing a device configured to cut hair according to claim 1; and directing the laser light through the cutting region, and towards a shaft of the hair to cut the hair.

27. The method of claim 26, further comprising preventing light from being emitted from the cutting region when the cutting region is not in contact with the hair.

* * * * *